(12) United States Patent
Harant

(10) Patent No.: US 11,034,726 B2
(45) Date of Patent: Jun. 15, 2021

(54) GENE EXPRESSION INHIBITORS

(71) Applicant: PIVARIS BIOSCIENCE GMBH, Vienna (AT)

(72) Inventor: Hanna Harant, Vienna (AT)

(73) Assignee: PIVARIS BIOSCIENCE GMBH, Vienna (AT)

( * ) Notice: Subject to any disclaimer, the term of this patent is extended or adjusted under 35 U.S.C. 154(b) by 0 days.

(21) Appl. No.: 16/646,450

(22) PCT Filed: Sep. 24, 2018

(86) PCT No.: PCT/EP2018/075817
§ 371 (c)(1),
(2) Date: Mar. 11, 2020

(87) PCT Pub. No.: WO2019/057973
PCT Pub. Date: Mar. 28, 2019

(65) Prior Publication Data
US 2020/0270305 A1 Aug. 27, 2020

(30) Foreign Application Priority Data

Sep. 24, 2017 (AT) .............. A 60096/2017
Jul. 16, 2018 (AT) .............. A 50613/2018

(51) Int. Cl.
*A61K 38/08* (2019.01)
*C07K 7/06* (2006.01)
*A61P 31/22* (2006.01)
*A61P 31/04* (2006.01)
*C07K 14/16* (2006.01)
*A61K 38/00* (2006.01)

(52) U.S. Cl.
CPC .............. *C07K 7/06* (2013.01); *A61P 31/04* (2018.01); *A61P 31/22* (2018.01); *C07K 14/16* (2013.01); *A61K 38/00* (2013.01); *C07K 2319/10* (2013.01)

(58) Field of Classification Search
None
See application file for complete search history.

(56) References Cited

U.S. PATENT DOCUMENTS

2004/0123343 A1\* 6/2004 La Rosa ............... C07K 14/415
800/278

FOREIGN PATENT DOCUMENTS

WO WO2014047261 3/2014

OTHER PUBLICATIONS

S.-J. Deng et al: "Identification of Peptides That Inhibit the DNA Binding, trans-Activator, and DNA Replication Functions of the Human Papillomavirus Type 11 E2 Protein", Journal of Virology., vol. 78, No. 5, Mar. 1, 2004 (Mar. 1, 2004), pp. 2637-2641.
Yongtao Xu et al: "Identification of Peptide Inhibitors of Enveloped Viruses Using Support Vector Machine", PLOS One, vol. 10, No. 11, Dec. 4, 2015 (Dec. 4, 2015).
International Search Report issued in PCT/EP2018/075817 dated Dec. 11, 2018.
Jacques Archambault et al: "Targeting human papillomavirus genome replication for antiviral drug discovery", Antiviral Therapy—An Official Publication of the International Society for Antiviral Research vol. 18,'No. 3, Apr. 23, 2013 (Apr. 23, 2013), pp. 271-283.

\* cited by examiner

*Primary Examiner* — Fred H Reynolds
(74) *Attorney, Agent, or Firm* — Workman Nydegger

(57) ABSTRACT

The present invention relates to a peptide comprising or consisting of an amino acid sequence according to formula (I) $X_1-X_2-X_3-X_4-X_5-(A)_m-X_6-X_7-(X_8)_n-C$ (I), wherein $X_1$ is C or S, $X_2$ is L or A, $X_3$ is A, V or L, $X_4$ is F or Y, $X_5$ is Y or F, $X_6$ is C or R, $X_7$ is F or L, $X_8$ is W or A and m and n are independently 0 or 1 or a variant thereof.

22 Claims, 14 Drawing Sheets
Specification includes a Sequence Listing.

SEQUENCE LISTING

```
<160> NUMBER OF SEQ ID NOS: 61

<210> SEQ ID NO 1
<211> LENGTH: 10
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (1)..(1)
<223> OTHER INFORMATION: Xaa is C or S
<220> FEATURE:
<221> NAME/KEY: misc_feature
<222> LOCATION: (2)..(2)
<223> OTHER INFORMATION: Xaa is L or A
<220> FEATURE:
<221> NAME/KEY: misc_feature
<222> LOCATION: (3)..(3)
<223> OTHER INFORMATION: Xaa is A, V or L
<220> FEATURE:
<221> NAME/KEY: misc_feature
<222> LOCATION: (4)..(4)
<223> OTHER INFORMATION: Xaa is F or Y
<220> FEATURE:
<221> NAME/KEY: misc_feature
<222> LOCATION: (5)..(5)
<223> OTHER INFORMATION: Xaa is F or Y
<220> FEATURE:
<221> NAME/KEY: misc_feature
<222> LOCATION: (6)..(6)
<223> OTHER INFORMATION: Xaa is A or no amino acid residue
<220> FEATURE:
<221> NAME/KEY: misc_feature
<222> LOCATION: (7)..(7)
<223> OTHER INFORMATION: Xaa is C or R
<220> FEATURE:
<221> NAME/KEY: misc_feature
<222> LOCATION: (8)..(8)
<223> OTHER INFORMATION: Xaa is F or L
<220> FEATURE:
<221> NAME/KEY: misc_feature
<222> LOCATION: (9)..(9)
<223> OTHER INFORMATION: Xaa is W, A or no amino acid residue

<400> SEQUENCE: 1

Xaa Xaa Xaa Xaa Xaa Xaa Xaa Xaa Xaa Cys
1               5                   10
```

```
<210> SEQ ID NO 2
<211> LENGTH: 10
<212> TYPE: PRT
<213> ORGANISM: Artificial Sequence
<220> FEATURE:
<223> OTHER INFORMATION: Peptide

<400> SEQUENCE: 2

Cys Leu Ala Phe Tyr Ala Cys Phe Trp Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Peptide

<400> SEQUENCE: 3

Cys Leu Ala Phe Tyr Ala Cys Leu Trp Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Peptide

<400> SEQUENCE: 4

Cys Leu Ala Phe Tyr Ala Cys Phe Ala Cys
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Peptide

<400> SEQUENCE: 5

Cys Leu Val Phe Tyr Ala Cys Phe Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Peptide

<400> SEQUENCE: 6

Cys Leu Ala Phe Tyr Ala Cys Phe Cys
1               5

<210> SEQ ID NO 7
<211> LENGTH: 8
<212> TYPE: PRT
<213> ORGANISM: Artificial Sequence
<220> FEATURE:
<223> OTHER INFORMATION: Peptide

<400> SEQUENCE: 7

Cys Leu Leu Tyr Phe Cys Phe Cys
1               5
```

```
<210> SEQ ID NO 8
<211> LENGTH: 9
<212> TYPE: PRT
<213> ORGANISM: Artificial Sequence
<220> FEATURE:
<223> OTHER INFORMATION: Peptide

<400> SEQUENCE: 8

Cys Ala Ala Phe Tyr Ala Cys Phe Cys
1               5

<210> SEQ ID NO 9
<211> LENGTH: 10
<212> TYPE: PRT
<213> ORGANISM: Artificial Sequence
<220> FEATURE:
<223> OTHER INFORMATION: Peptide

<400> SEQUENCE: 9

Ser Leu Ala Phe Tyr Ala Cys Phe Ala Cys
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Peptide

<400> SEQUENCE: 10

Cys Leu Ala Phe Tyr Ala Arg Phe Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Peptide

<400> SEQUENCE: 11

Cys Leu Ala Phe Tyr Cys Phe Ala Cys
1               5

<210> SEQ ID NO 12
<211> LENGTH: 8
<212> TYPE: PRT
<213> ORGANISM: Artificial Sequence
<220> FEATURE:
<223> OTHER INFORMATION: Peptide

<400> SEQUENCE: 12

Cys Leu Ala Phe Tyr Cys Phe Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Peptide

<400> SEQUENCE: 13

Cys Leu Ala Tyr Phe Cys Phe Cys
1               5
```

```
<210> SEQ ID NO 14
<211> LENGTH: 86
<212> TYPE: PRT
<213> ORGANISM: Artificial Sequence
<220> FEATURE:
<223> OTHER INFORMATION: Peptide

<400> SEQUENCE: 14

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
            20                  25                  30

His Cys Gln Val Cys Phe Thr Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Gly Pro Lys Glu
                85

<210> SEQ ID NO 15
<211> LENGTH: 13
<212> TYPE: PRT
<213> ORGANISM: Artificial Sequence
<220> FEATURE:
<223> OTHER INFORMATION: Peptide

<400> SEQUENCE: 15

Gly Arg Lys Lys Arg Arg Gln Arg Arg Pro Pro Gln
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Peptide

<400> SEQUENCE: 16

Tyr Gly Arg Lys Lys Arg Arg Gln Arg Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Peptide

<400> SEQUENCE: 17

Cys Tyr Gly Arg Lys Lys Arg Arg Gln Arg Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Peptide

<400> SEQUENCE: 18

Tyr Gly Arg Lys Lys Arg Arg Gln Arg Arg Gly Gly Gly
1               5                   10
```

```
<210> SEQ ID NO 19
<211> LENGTH: 11
<212> TYPE: PRT
<213> ORGANISM: Artificial Sequence
<220> FEATURE:
<223> OTHER INFORMATION: Peptide

<400> SEQUENCE: 19

Cys Gly Arg Lys Lys Arg Arg Gln Arg Arg Arg
1               5                   10

<210> SEQ ID NO 20
<211> LENGTH: 22
<212> TYPE: PRT
<213> ORGANISM: Artificial Sequence
<220> FEATURE:
<223> OTHER INFORMATION: Peptide

<400> SEQUENCE: 20

Gly Arg Lys Lys Arg Arg Gln Arg Arg Pro Pro Gln Cys Leu Ala
1               5                   10                  15

Phe Tyr Ala Cys Phe Cys
            20

<210> SEQ ID NO 21
<211> LENGTH: 16
<212> TYPE: PRT
<213> ORGANISM: Artificial Sequence
<220> FEATURE:
<223> OTHER INFORMATION: Peptide

<400> SEQUENCE: 21

Arg Gln Ile Lys Ile Trp Phe Gln Asn Arg Arg Met Lys Trp Lys Lys
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: Peptide

<400> SEQUENCE: 22

Arg Arg Arg Arg Arg Arg Arg
1               5

<210> SEQ ID NO 23
<211> LENGTH: 8
<212> TYPE: PRT
<213> ORGANISM: Artificial Sequence
<220> FEATURE:
<223> OTHER INFORMATION: Peptide

<400> SEQUENCE: 23

Arg Arg Arg Arg Arg Arg Arg Cys
1               5

<210> SEQ ID NO 24
<211> LENGTH: 8
<212> TYPE: PRT
<213> ORGANISM: Artificial Sequence
<220> FEATURE:
<223> OTHER INFORMATION: Peptide

<400> SEQUENCE: 24

Arg Arg Arg Arg Arg Arg Arg Arg
1               5
```

```
<210> SEQ ID NO 25
<211> LENGTH: 9
<212> TYPE: PRT
<213> ORGANISM: Artificial Sequence
<220> FEATURE:
<223> OTHER INFORMATION: Peptide

<400> SEQUENCE: 25

Arg Arg Arg Arg Arg Arg Arg Arg Arg
1               5

<210> SEQ ID NO 26
<211> LENGTH: 21
<212> TYPE: PRT
<213> ORGANISM: Artificial Sequence
<220> FEATURE:
<223> OTHER INFORMATION: Peptide

<400> SEQUENCE: 26

Thr Arg Ser Ser Arg Ala Gly Leu Gln Phe Pro Val Gly Arg Val His
1               5                   10                  15

Arg Leu Leu Arg Lys
            20

<210> SEQ ID NO 27
<211> LENGTH: 27
<212> TYPE: PRT
<213> ORGANISM: Artificial Sequence
<220> FEATURE:
<223> OTHER INFORMATION: Peptide

<400> SEQUENCE: 27

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 28
<211> LENGTH: 30
<212> TYPE: PRT
<213> ORGANISM: Artificial Sequence
<220> FEATURE:
<223> OTHER INFORMATION: Peptide

<400> SEQUENCE: 28

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 29
<211> LENGTH: 18
<212> TYPE: PRT
<213> ORGANISM: Artificial Sequence
<220> FEATURE:
<223> OTHER INFORMATION: Peptide

<400> SEQUENCE: 29

Lys Leu Ala Leu Lys Leu Ala Leu Lys Ala Leu Lys Ala Ala Leu Lys
1               5                   10                  15

Leu Ala
```

```
<210> SEQ ID NO 30
<211> LENGTH: 21
<212> TYPE: PRT
<213> ORGANISM: Artificial Sequence
<220> FEATURE:
<223> OTHER INFORMATION: Peptide

<400> SEQUENCE: 30

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 31
<211> LENGTH: 24
<212> TYPE: PRT
<213> ORGANISM: Artificial Sequence
<220> FEATURE:
<223> OTHER INFORMATION: Peptide

<400> SEQUENCE: 31

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 32
<211> LENGTH: 18
<212> TYPE: PRT
<213> ORGANISM: Artificial Sequence
<220> FEATURE:
<223> OTHER INFORMATION: Peptide

<400> SEQUENCE: 32

Leu Leu Ile Ile Leu Arg Arg Arg Ile Arg Lys Gln Ala His Ala His
1               5                   10                  15

Ser Lys

<210> SEQ ID NO 33
<211> LENGTH: 16
<212> TYPE: PRT
<213> ORGANISM: Artificial Sequence
<220> FEATURE:
<223> OTHER INFORMATION: Peptide

<400> SEQUENCE: 33

Arg Val Ile Arg Val Trp Phe Gln Asn Lys Arg Cys Lys Asp Lys Lys
1               5                   10                  15

<210> SEQ ID NO 34
<211> LENGTH: 27
<212> TYPE: PRT
<213> ORGANISM: Artificial Sequence
<220> FEATURE:
<223> OTHER INFORMATION: Peptide

<400> SEQUENCE: 34

Arg Gln Gly Ala Ala Arg Val Thr Ser Trp Leu Gly Arg Gln Leu Arg
1               5                   10                  15

Ile Ala Gly Lys Arg Leu Glu Gly Arg Ser Lys
            20                  25
```

```
<210> SEQ ID NO 35
<211> LENGTH: 13
<212> TYPE: PRT
<213> ORGANISM: Artificial Sequence
<220> FEATURE:
<223> OTHER INFORMATION: Peptide

<400> SEQUENCE: 35

Lys Leu Ile Lys Gly Arg Thr Pro Ile Lys Phe Gly Lys
1               5                   10

<210> SEQ ID NO 36
<211> LENGTH: 27
<212> TYPE: PRT
<213> ORGANISM: Artificial Sequence
<220> FEATURE:
<223> OTHER INFORMATION: Peptide

<400> SEQUENCE: 36

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 37
<211> LENGTH: 12
<212> TYPE: PRT
<213> ORGANISM: Artificial Sequence
<220> FEATURE:
<223> OTHER INFORMATION: Peptide

<400> SEQUENCE: 37

Pro Lys Lys Lys Arg Lys Val Glu Asp Pro Tyr Cys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Peptide

<400> SEQUENCE: 38

Cys Gly Gly Gly Pro Lys Lys Lys Arg Lys Val Glu Asp
1               5                   10

<210> SEQ ID NO 39
<211> LENGTH: 29
<212> TYPE: PRT
<213> ORGANISM: Artificial Sequence
<220> FEATURE:
<223> OTHER INFORMATION: Peptide

<400> SEQUENCE: 39

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 40
<211> LENGTH: 21
<212> TYPE: PRT
<213> ORGANISM: Artificial Sequence
<220> FEATURE:
<223> OTHER INFORMATION: Peptide
```

```
<400> SEQUENCE: 40

Cys Leu Ala Phe Tyr Ala Cys Phe Cys Gly Gly Gly Cys Leu Ala Phe
1               5                   10                  15

Tyr Ala Cys Phe Cys
            20

<210> SEQ ID NO 41
<211> LENGTH: 9
<212> TYPE: PRT
<213> ORGANISM: Artificial Sequence
<220> FEATURE:
<223> OTHER INFORMATION: Peptide

<400> SEQUENCE: 41

Ser Ala Phe Tyr Ala Cys Phe Ala Cys
1               5

<210> SEQ ID NO 42
<211> LENGTH: 9
<212> TYPE: PRT
<213> ORGANISM: Artificial Sequence
<220> FEATURE:
<223> OTHER INFORMATION: Peptide

<400> SEQUENCE: 42

Cys Leu Ala Phe Tyr Arg Cys Phe Cys
1               5

<210> SEQ ID NO 43
<211> LENGTH: 9
<212> TYPE: PRT
<213> ORGANISM: Artificial Sequence
<220> FEATURE:
<223> OTHER INFORMATION: Peptide

<400> SEQUENCE: 43

Ser Leu Ala Phe Tyr Ala Ser Phe Ser
1               5

<210> SEQ ID NO 44
<211> LENGTH: 6
<212> TYPE: PRT
<213> ORGANISM: Artificial Sequence
<220> FEATURE:
<223> OTHER INFORMATION: Peptide

<400> SEQUENCE: 44

Phe Tyr Ala Cys Phe Cys
1               5

<210> SEQ ID NO 45
<211> LENGTH: 7
<212> TYPE: PRT
<213> ORGANISM: Artificial Sequence
<220> FEATURE:
<223> OTHER INFORMATION: Peptide

<400> SEQUENCE: 45

Phe Tyr Ala Cys Phe Ala Cys
1               5

<210> SEQ ID NO 46
<211> LENGTH: 5
<212> TYPE: PRT
<213> ORGANISM: Artificial Sequence
```

```
<220> FEATURE:
<223> OTHER INFORMATION: Peptide

<400> SEQUENCE: 46

Phe Tyr Cys Phe Cys
1               5

<210> SEQ ID NO 47
<211> LENGTH: 7
<212> TYPE: PRT
<213> ORGANISM: Artificial Sequence
<220> FEATURE:
<223> OTHER INFORMATION: Peptide

<400> SEQUENCE: 47

Cys Leu Ala Phe Tyr Ala Cys
1               5

<210> SEQ ID NO 48
<211> LENGTH: 9
<212> TYPE: PRT
<213> ORGANISM: Artificial Sequence
<220> FEATURE:
<223> OTHER INFORMATION: Peptide

<400> SEQUENCE: 48

Cys Leu Ala Phe Arg Ala Cys Phe Cys
1               5

<210> SEQ ID NO 49
<211> LENGTH: 9
<212> TYPE: PRT
<213> ORGANISM: Artificial Sequence
<220> FEATURE:
<223> OTHER INFORMATION: Peptide

<400> SEQUENCE: 49

Cys Leu Ala Phe Tyr Ala Cys Arg Cys
1               5

<210> SEQ ID NO 50
<211> LENGTH: 6
<212> TYPE: PRT
<213> ORGANISM: Artificial Sequence
<220> FEATURE:
<223> OTHER INFORMATION: Peptide

<400> SEQUENCE: 50

Phe Tyr Cys Phe Ala Cys
1               5

<210> SEQ ID NO 51
<211> LENGTH: 9
<212> TYPE: PRT
<213> ORGANISM: Artificial Sequence
<220> FEATURE:
<223> OTHER INFORMATION: Peptide

<400> SEQUENCE: 51

Cys Leu Ala Arg Tyr Ala Cys Phe Cys
1               5

<210> SEQ ID NO 52
<211> LENGTH: 8
<212> TYPE: PRT
<213> ORGANISM: Artificial Sequence
```

-continued

```
<220> FEATURE:
<223> OTHER INFORMATION: Peptide

<400> SEQUENCE: 52

Ser Val Phe Tyr Ala Cys Phe Cys
1               5

<210> SEQ ID NO 53
<211> LENGTH: 9
<212> TYPE: PRT
<213> ORGANISM: Artificial Sequence
<220> FEATURE:
<223> OTHER INFORMATION: Peptide

<400> SEQUENCE: 53

Cys Pro Ser Ala Leu Ala Phe Tyr Cys
1               5

<210> SEQ ID NO 54
<211> LENGTH: 10
<212> TYPE: PRT
<213> ORGANISM: Artificial Sequence
<220> FEATURE:
<223> OTHER INFORMATION: Peptide

<400> SEQUENCE: 54

Trp Ser Glu Gln Cys Phe Thr Cys Trp Trp
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Peptide

<400> SEQUENCE: 55

Ser Val Phe Tyr Ala Cys Phe Ala Cys
1               5

<210> SEQ ID NO 56
<211> LENGTH: 9
<212> TYPE: PRT
<213> ORGANISM: Artificial Sequence
<220> FEATURE:
<223> OTHER INFORMATION: Peptide

<400> SEQUENCE: 56

Cys Ser Leu Thr Gly Pro Ile Ala Cys
1               5

<210> SEQ ID NO 57
<211> LENGTH: 16
<212> TYPE: PRT
<213> ORGANISM: Artificial Sequence
<220> FEATURE:
<223> OTHER INFORMATION: Peptide

<400> SEQUENCE: 57

Glu Asp Gly Gly Ser Phe Met Cys Leu Trp Cys Gly Glu Val His Gly
1               5                   10                  15

<210> SEQ ID NO 58
<211> LENGTH: 7
<212> TYPE: PRT
<213> ORGANISM: Artificial Sequence
```

-continued

```
<220> FEATURE:
<223> OTHER INFORMATION: Peptide

<400> SEQUENCE: 58

Pro Ser Ala Leu Ala Phe Tyr
1               5

<210> SEQ ID NO 59
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (2)..(2)
<223> OTHER INFORMATION: Xaa is L or A
<220> FEATURE:
<221> NAME/KEY: misc_feature
<222> LOCATION: (3)..(3)
<223> OTHER INFORMATION: Xaa is A, V or L
<220> FEATURE:
<221> NAME/KEY: misc_feature
<222> LOCATION: (4)..(4)
<223> OTHER INFORMATION: Xaa is F or Y
<220> FEATURE:
<221> NAME/KEY: misc_feature
<222> LOCATION: (5)..(5)
<223> OTHER INFORMATION: Xaa is Y or F
<220> FEATURE:
<221> NAME/KEY: misc_feature
<222> LOCATION: (6)..(6)
<223> OTHER INFORMATION: Xaa is A or no amino acid residue (i.e. a bond)
<220> FEATURE:
<221> NAME/KEY: misc_feature
<222> LOCATION: (8)..(8)
<223> OTHER INFORMATION: Xaa is F or L
<220> FEATURE:
<221> NAME/KEY: misc_feature
<222> LOCATION: (9)..(9)
<223> OTHER INFORMATION: Xaa is W, A or no amino acid residue (i.e. a
      bond)

<400> SEQUENCE: 59

Cys Xaa Xaa Xaa Xaa Xaa Cys Xaa Xaa Cys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (1)..(1)
<223> OTHER INFORMATION: Xaa is C or S
<220> FEATURE:
<221> NAME/KEY: misc_feature
<222> LOCATION: (2)..(2)
<223> OTHER INFORMATION: Xaa is L or A
<220> FEATURE:
<221> NAME/KEY: misc_feature
<222> LOCATION: (3)..(3)
<223> OTHER INFORMATION: Xaa is A, V or L
<220> FEATURE:
<221> NAME/KEY: misc_feature
<222> LOCATION: (4)..(4)
<223> OTHER INFORMATION: Xaa is F or Y
<220> FEATURE:
<221> NAME/KEY: misc_feature
<222> LOCATION: (5)..(5)
<223> OTHER INFORMATION: Xaa is Y or F
```

```
<220> FEATURE:
<221> NAME/KEY: misc_feature
<222> LOCATION: (6)..(6)
<223> OTHER INFORMATION: Xaa is A or no amino acid residue
<220> FEATURE:
<221> NAME/KEY: misc_feature
<222> LOCATION: (8)..(8)
<223> OTHER INFORMATION: Xaa is F or L
<220> FEATURE:
<221> NAME/KEY: misc_feature
<222> LOCATION: (9)..(9)
<223> OTHER INFORMATION: Xaa is W, A or no amino acid residue

<400> SEQUENCE: 60

Xaa Xaa Xaa Xaa Xaa Xaa Cys Xaa Xaa Cys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (3)..(3)
<223> OTHER INFORMATION: Xaa is A, V or L
<220> FEATURE:
<221> NAME/KEY: misc_feature
<222> LOCATION: (4)..(4)
<223> OTHER INFORMATION: Xaa is F or Y
<220> FEATURE:
<221> NAME/KEY: misc_feature
<222> LOCATION: (5)..(5)
<223> OTHER INFORMATION: Xaa is Y or F
<220> FEATURE:
<221> NAME/KEY: misc_feature
<222> LOCATION: (6)..(6)
<223> OTHER INFORMATION: Xaa is A or no amino acid residue
<220> FEATURE:
<221> NAME/KEY: misc_feature
<222> LOCATION: (8)..(8)
<223> OTHER INFORMATION: Xaa is F or L
<220> FEATURE:
<221> NAME/KEY: misc_feature
<222> LOCATION: (9)..(9)
<223> OTHER INFORMATION: Xaa is W, A or no amino acid residue

<400> SEQUENCE: 61

Cys Leu Xaa Xaa Xaa Xaa Cys Xaa Xaa Cys
1               5                   10
```

GENE EXPRESSION INHIBITORS

SEQUENCE LISTING

The instant application contains a Sequence Listing that has been submitted electronically in ASCII format and is hereby incorporated by reference in its entirety. Said ASCII copy, created on Mar. 11, 2020, is named "16785-242_2020-03-11_Sequence-Listing_ST25" and is 15.7 kb in size.

TECHNICAL FIELD

The present invention relates to peptides and compounds influencing the transcription and translation of nucleic acid molecules within an organism, cell or tissue.

BACKGROUND ART

The genomic DNA of a eukaryotic cell is localized in the nucleus and tightly packed into chromosomes. Transcription of DNA into RNA takes place in the nucleus followed by export of the RNA to the cytosol where protein synthesis occurs at the ribosomes. In contrast, "foreign" DNA, or also called extrachromosomal, exogenous or heterologous DNA is defined as non-self DNA which is normally not present in the target cell and can enter the cells from outside the cell. The "foreign" DNA molecule can be for instance a plasmid-DNA, a PCR product, a synthetic DNA, a viral or phage DNA, a bacterial DNA or any other engineered DNA. An RNA can be also a "foreign" nucleic acid, for instance provided by an RNA virus.

Transfer of non-self DNA, such as "foreign" DNA molecules, for instance from viruses or between bacteria can occur in eukaryotic or prokaryotic target cells where the DNA molecule enters a cell and can be integrated into the host genome, or the host cellular machinery is used for its own replication, transcription and translation of the "foreign" DNA-encoded proteins. A "foreign" DNA can be taken up by endocytosis or by other means such as packed in a virus, and passages the cytosol either naked or within a virus before entering the target cells' nucleus. Viral DNA can be unpacked in the cytosol at the site of nuclear import.

In eukaryotes, there are host-cell defense mechanisms for recognition of "foreign" nucleic acids including pattern recognition receptors, for instance Toll-like receptors and other nucleic acid sensing molecules. These mechanisms represent the innate immune system leading to a first response against a viral or bacterial infection and activation of a cascade of subsequent events to eliminate the infection.

Prevention or treatment of viral infections is still a major obstacle. Prevention of viral infections by vaccination is limited to specific viruses, while curative treatment of already established viral infections is often not possible. In addition, viruses are prone to mutations and can therefore escape already established preventive or curative treatments. Moreover, only for some viral infections, drugs are available which can reduce or even eliminate a virus in an infected individual. A virus requires a host cell for its own replication.

For instance, modes of interference with herpes virus infections is the use of different types of inhibitors, such as the nucleoside analogs aciclovir or ganciclovir, DNA polymerase inhibitors, such as foscarnet, or primase/helicase inhibitors such as pritelivir. Other antivirals include entry inhibitors such as amantadine or enfuvirtide or protease inhibitors for treatment of influenza or HIV. However, there are no inhibitors which can distinguish between genomic and "foreign" DNA. Management of virus-specific gene expression could be therefore one possible mode of intervention to inhibit early viral gene expression and subsequent viral replication in the host organism.

SUMMARY OF THE INVENTION

It is an object of the present invention to provide compounds, which are capable to inhibit transcription and/or translation of foreign (i.e. heterologous or exogenous) nucleic acid molecules, including genes (inhibition of gene expression), in organisms.

This object is achieved by a peptide comprising or consisting of an amino acid sequence according to formula I (SEQ ID No. 1)

$$X_1\text{-}X_2\text{-}X_3\text{-}X_4\text{-}X_5\text{-}(A)_m\text{-}X_6\text{-}X_7\text{-}(X_8)_n\text{-}C \qquad (I)$$

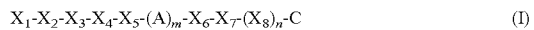

wherein $X_1$ is C or S, $X_2$ is L or A, $X_3$ is A, V or L, $X_4$ is F or Y, $X_5$ is Y or F, $X_6$ is C or R, $X_7$ is F or L, $X_8$ is W or A and m and n are independently 0 or 1.

The present invention relates also to a peptidic compound comprising at least one peptide comprising or consisting of formula I (SEQ ID No. 1)

$$X_1\text{-}X_2\text{-}X_3\text{-}X_4\text{-}X_5\text{-}(A)_m\text{-}X_6\text{-}X_7\text{-}(X_8)_n\text{-}C \qquad (I)$$

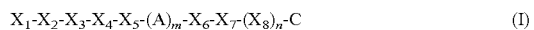

wherein $X_1$ is C or S, $X_2$ is L or A, $X_3$ is A, V or L, $X_4$ is F or Y, $X_5$ is Y or F, $X_6$ is C or R, $X_7$ is F or L, $X_8$ is W or A and m and n are independently 0 or 1.

It turned surprisingly out that the peptides and peptidic compounds of the present invention are able to inhibit transcription and/or translation of foreign/heterologous/exogenous nucleic acid molecules and/or gene expression from the foreign DNA molecules in cells while not affecting expression of cellular genes naturally occurring in said cells. Hence, this inhibition is not or substantially not cytotoxic.

The capability of the peptides and compounds of the present invention to inhibit or to reduce significantly the translation and/or transcription of heterologous nucleic acid molecules within an organism (i.e. living cell) allows the treatment and/or prevention of diseases which are associated with the translation and/or transcription of foreign nucleic acid molecules.

Thus, another aspect of the present invention relates to a peptide and/or compound according to the present invention for the use in the treatment of viral, bacterial, parasitic or fungal infections in a mammal or human individual.

A further aspect of the present invention relates to a nucleic acid molecule encoding a peptide or compound according to the present invention.

Another aspect of the present invention relates to a peptide and/or compound according to present invention for inhibiting transcription and/or translation of a heterologous nucleic acid molecule in a cell.

A further aspect of the present invention relates to the use of peptides and/or compound according to the present invention for preventing bacterial cells to gain genes or functional fragments thereof capable to provide antibiotic resistance to said bacterial cells.

Another aspect of the present invention relates to the use of a peptide and/or compound according to the present invention as an additive for an attenuated live vaccine.

A further aspect of the present invention relates to the use of a peptide and/or compound according to the present invention to inhibit or prevent viral spread in cell cultures.

Yet another aspect of the present invention relates to the use of a peptide and/or compound of the present invention to inhibit phage infection of bacteria.

A further aspect of the present invention relates to the use of a peptide and/or compound according to the present invention to localize the transcription and/or translation of a heterologous nucleic acid molecule within a eukaryotic cell.

DETAILED DESCRIPTION OF EMBODIMENTS

Figure 1:
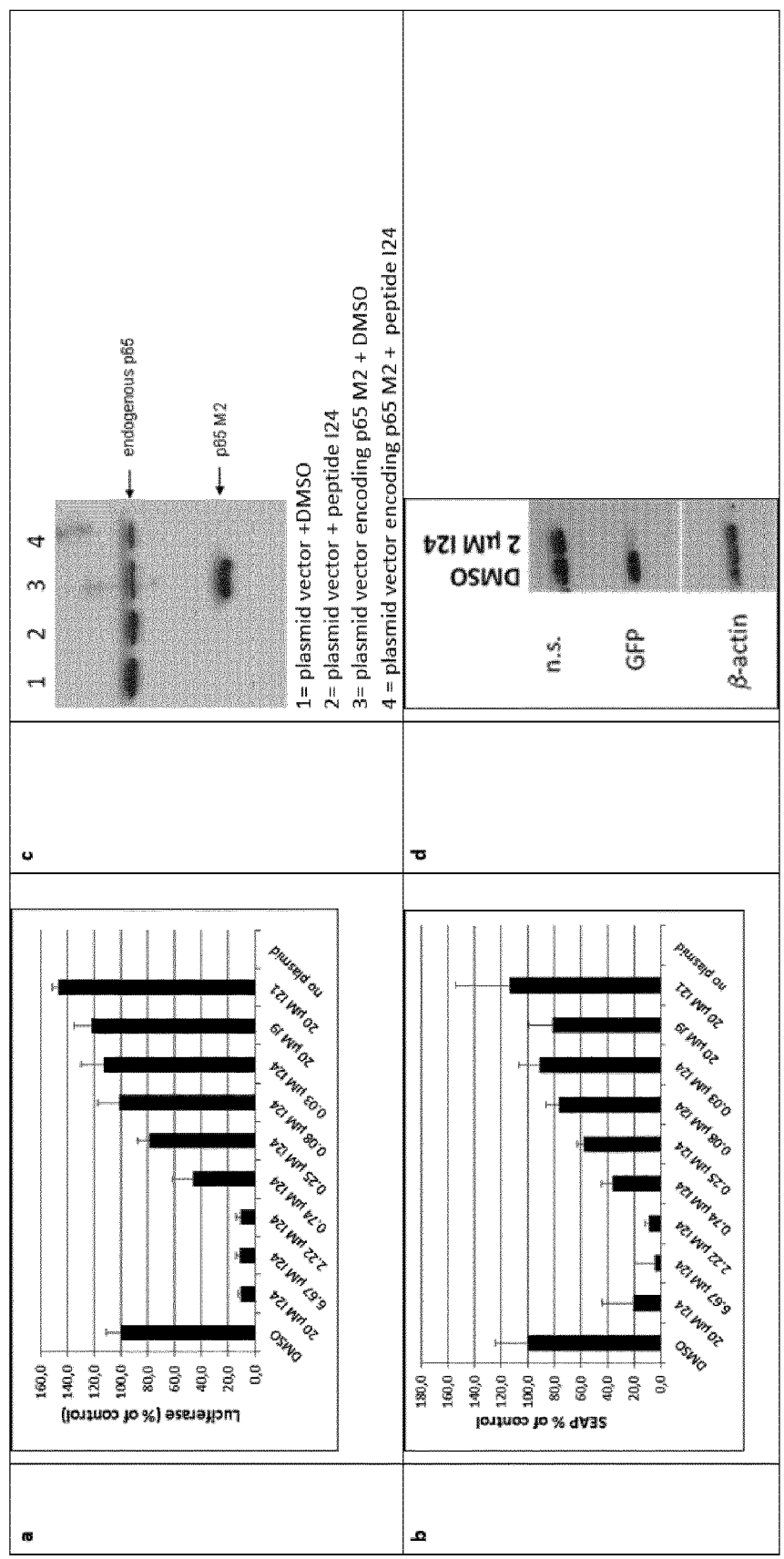
FIG. 1. Effects of peptide I24 on production of luciferase levels (a) and SEAP release (b) in cells transfected with plasmid vectors encoding these proteins. Effect of peptide I24 on expression p65 mutant M2 when transfected with the plasmid encoding p65 M2 (FIG. 1c). Effect of peptide on expression of GFP and number of GFP-positive cells when transfected with the plasmid encoding GFP (FIG. 1d, e).
Figure 1:
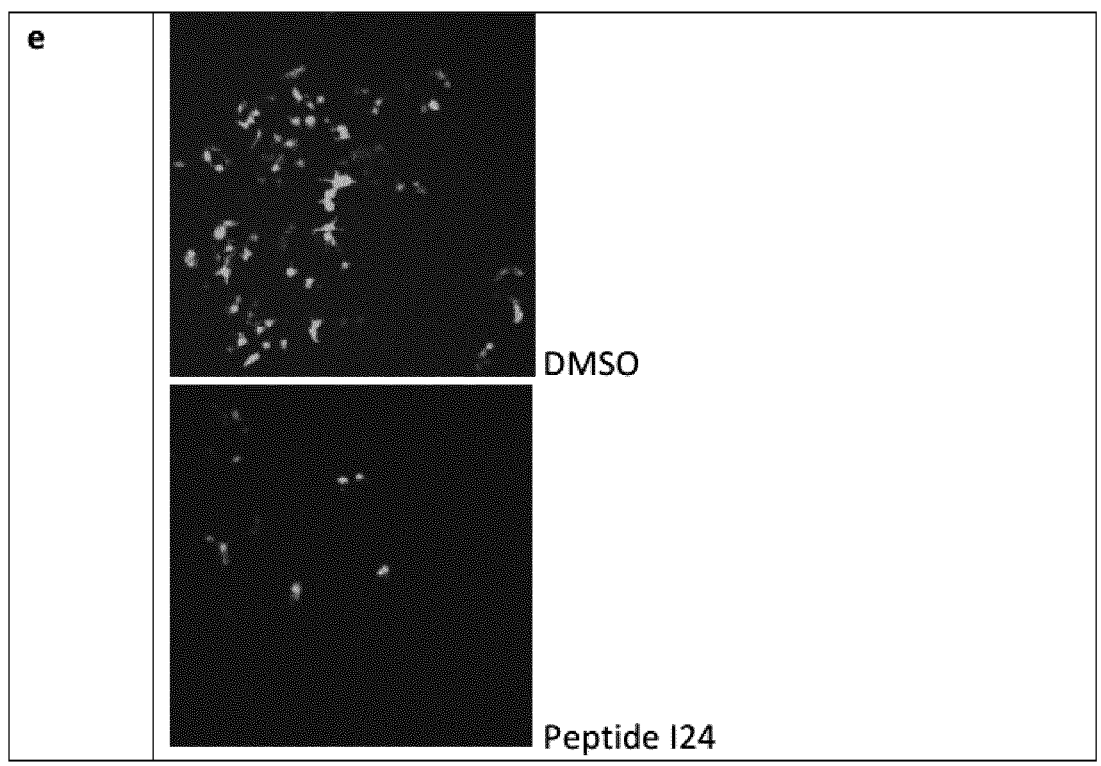

The present invention relates to a peptide comprising or consisting of an amino acid sequence according to formula I (SEQ ID No. 1)

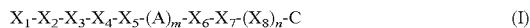

$$X_1\text{-}X_2\text{-}X_3\text{-}X_4\text{-}X_5\text{-}(A)_m\text{-}X_6\text{-}X_7\text{-}(X_8)_n\text{-}C \quad (I)$$

wherein $X_1$ is C or S, $X_2$ is L or A, $X_3$ is A, V or L, $X_4$ is F or Y, $X_5$ is Y or F, $X_6$ is C or R, $X_7$ is F or L, $X_8$ is W or A and m and n are independently 0 or 1 or a variant thereof.

As mentioned above the peptides of the present invention are able to inhibit transcription and/or translation of foreign/heterologous/exogenous nucleic acid molecules and/or gene expression from the foreign DNA molecules in cells while not affecting expression of cellular genes naturally occurring in said cells.

According to a preferred embodiment of the present invention, the invention provides a peptide which can inhibit gene expression from the "foreign" DNA while not affecting gene expression of cellular-genome encoded proteins. While the peptide I24 can inhibit luciferase expression under control of the interleukin-8 promoter when transfected together with a plasmid encoding luciferase under control of the interleukin-8 promoter and further stimulation with tumor necrosis factor-α (TNF-α), endogenous levels of TNF-α-induced interleukin-8 remained unaffected.

"Foreign nucleic acid molecule" (i.e. heterologous or exogenous nucleic acid molecule), as used herein, refers to a nucleic acid molecule which is not naturally occurring in an organism or cell and is usually introduced into this organism or cell by methods known in the art, including cell fusion, viral infections, and other common methods known in the art (e.g. electroporation).

Transfer of "foreign" DNA can occur by means of transfection of eukaryotic cells using liposomal, nonliposomal, electroporation or other transfection procedures known in the art but also by natural transfer mechanisms such as by viral or phage infection or DNA transfer between bacteria or other organisms. The "foreign" DNA can be also transferred to prokaryotic cells by transformation procedures known in the art or by natural transfer such as horizontal gene transfer.

"Foreign" nucleic acid, extrachromosomal, heterologous or exogenous nucleic acid, is not normally present in the target cell and can be a plasmid, a PCR product or any other synthetic DNA or RNA, or a nucleic acid packed in a virus or phage or derived from organisms such as bacteria, protozoa or fungi and is "foreign" to the target cell. Said DNA molecules or organisms or viruses harboring DNA can be transferred to the target cell by chemical or biological means, by endocytosis, infection or invasion. A target cell can be eukaryotic, mammalian, vertebrate or invertebrate cell, a plant cell, a bacterium belonging to the eubacteria or archaebacteria, fungi or protozoa.

According to a preferred embodiment of the present invention the "foreign" nucleic acid represents preferentially a DNA molecule, most preferentially a double-stranded DNA molecule but can be also an RNA molecule or a DNA molecule associated with RNA. The "foreign" DNA can be a supercoiled or linear DNA and can be a plasmid-DNA or a PCR product or an oligonucleotide. The "foreign" nucleic acid can be part of the genome of the infecting agent or extrachromosomal DNA derived from bacteria, phages, viruses, fungi or parasites such as protozoa or helminths.

The expression plasmid-DNA for transfection of eukaryotic cells can contain specific elements, such as a eukaryotic promoter driving expression of the encoded gene (such as a CMV or SV40 promoter) by RNA polymerase II. It further contains elements such as a polyadenylation site, a ribosome priming site and optionally a eukaryotic origin of replication. It can also contain a T7 promoter for sequencing or for in vitro expression with T7 polymerase. For plasmid propagation in bacteria, the expression plasmid can also contain a bacterial origin of replication, an antibiotic resistance gene for selection and a prokaryotic promoter driving expression of the antibiotic resistance gene.

A "foreign" DNA can be provided by a virus, such as a natural occurring DNA virus or an engineered virus for gene transfer. A double-stranded DNA virus has a viral genome represented as double stranded DNA. Double-stranded DNA viruses belong to the families Adenoviridae, Herpesviridae and Polyoamviridae, Papillomaviridae, Caudovirales, Ligamenvirales, Baculo-like viruses, such as Baculoviridae, and Nucleo-Cytoplasmic Large DNA viruses belonging to the family of Poxviridae. Another family with a circular, partially, double-stranded DNA belong to the family of Hepadnaviridae, represented by hepatitis B virus where circular DNA is transported to the nucleus and transcribed, followed by a reverse-transcription of the synthesized pregenomic RNA. Other classes of viruses are single-stranded DNA viruses, and RNA viruses, containing single- or double stranded RNA. A "foreign" DNA can be also a phage DNA. Phages with a double-stranded DNA genome belong to families of the Myoviridae, Siphoviridae, Podoviridae, Tectiviridae, Corticoviridae, Plasmaviridae, Lipothrixviridae, Rudiviridae, Fuselloviridae, Salterprovirus, or Guttaviridae. Examples for viral vectors for gene transduction used in biomolecular research or technology are vaccinia virus, adenovirus, herpes simplex virus, baculovirus, lentivirus or adeno-associated virus.

One application of the peptide and compound of the present invention could therefore be prevention of early gene expression from a viral DNA leading to a subsequent reduction or inhibition of viral replication.

In contrast to prevention of "foreign"-DNA transfer and gene expression, the peptide and compound of the present invention may be also useful in situations of intended gene expression such by gene transfer during gene therapy. Said inhibitor could be useful for selective gene expression from the transgene in a specific target cell type by excluding gene expression in other cell types treated with inhibitor.

A target cell of the peptide and compound of the present invention can be a eukaryotic cell, such as a primary cell or cells within a tissue but can be also a cell line, either an immortalized tumor-derived cell line or engineered cell line or immortalized by other means, such as by a virus. The target cell can be of mammalian, including human, origin, but can also be of vertebrate or invertebrate origin, such as an insect cell. The target cell can be also a prokaryotic or archaea cell such as bacteria or archaea.

As shown in the examples and according to a preferred embodiment of the present invention, the peptides of the present invention, in particular peptide I24, inhibit mRNA levels from cells transfected with expression plasmid and peptide simultaneously exemplified by the reduction of luciferase mRNA levels in cells transfected with a luciferase expression plasmid and peptide simultaneously. The reduction of mRNA levels and protein levels have a comparable time- and dose-dependence. Inhibition of mRNA levels in transfected cells may be through direct contact between the peptide and the DNA molecule thereby preventing subsequent steps in RNA transcription or by inhibition of a DNA-dependent RNA polymerase activity or by inhibiting binding or interaction of host factors with the DNA molecule involved in transactivation such as a transcription factor, a factor associated with a transcription factor or a factor involved in general transcription activation for instance a TATA-box binding protein or related factor. Interaction with the DNA may already occur in the membrane or cytoplasm before the DNA molecule enters the nucleus. Albeit unlikely, the inhibitor may act at a post-transcriptional level affecting mRNA stability.

As shown in the examples, the peptides of the present invention, in particular peptide I24, inhibit protein levels in expression plasmid-transfected eukaryotic cells independent of certain elements of the expression plasmid. The inhibition is independent of the type of bacterial or eukaryotic antibiotic resistance gene. The inhibition of protein production by the peptide in eukaryotic cells is partially dependent on the type of eukaryotic promoter present in the expression plasmid. The promoter can be for instance a cytomegalovirus (CMV) promoter or a natural eukaryotic promoter, such as the interleukin-8 (CXCL-8) promoter or a synthetic promoter, such as a minimal promoter with elements such as NF-KB binding sites, driving transcription. A gene under control of the SV40 early promoter is less potently inhibited by the peptide I24 compared to luciferase under control of the CMV promoter.

According to a preferred embodiment of the present invention the N-terminus of the peptide of the present invention can be an amine, the C-terminus can be an amide or acid.

The peptide and compound of the present invention can be generated by classical peptide synthesis and is soluble in dimethyl sulfoxide (DMSO) but may be soluble in other solvents, such as aqueous solutions, alcohols, organic solvents, or emulsions.

The peptides of the present invention can also be considered to be "inhibitors" because the peptides "inhibit" or even prevent the transcription and/or translation of foreign nucleic acid molecules.

Another aspect of the present invention relates to a peptidic compound comprising at least one peptide comprising or consisting of formula I (SEQ ID No. 1)

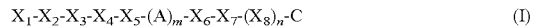

$$X_1\text{-}X_2\text{-}X_3\text{-}X_4\text{-}X_5\text{-}(A)_m\text{-}X_6\text{-}X_7\text{-}(X_8)_n\text{-}C \qquad (I)$$

wherein $X_1$ is C or S, $X_2$ is L or A, $X_3$ is A, V or L, $X_4$ is F or Y, $X_5$ is Y or F, $X_6$ is C or R, $X_7$ is F or L, $X_8$ is W or A and m and n are independently 0 or 1 or a variant thereof.

"Peptidic compound", as used herein, refers to a compound comprising amino acid residues which are linked to each other by a peptide bond (i.e. amide bond) forming a chain of amino acid residues. A "peptidic compound" according to the present invention comprises at least one peptide comprising or consisting of formula I. The peptidic compound may comprise next to the at least one peptide of the present invention other chemical moieties like proteins, polysaccharides, fatty acids such as palmitic acid, lipids, combinations thereof including lipoproteins and glycolipids, nucleic acids (e.g. DNA, siRNA, shRNA, antisense oligonucleotides), small molecule drugs (e.g. nucleoside analogs, helicase inhibitors) and imaging agents (e.g. fluorophore, quantum dots, radioactive tracers, metal chelates).

"Compound", as used herein, can be a polypeptide or peptide or any other chemical substance being conjugated or bound to the at least one peptide comprising or consisting of formula (I). Thus, a "peptidic compound" of the present invention can be either a fusion polypeptide, peptide or protein or a conjugate or a combination thereof.

A "variant" of the at least one peptide comprising or consisting of formula I may comprise at least one, preferably at least two, more preferably at least three, up to a maximum of five, preferably up to a maximum of four, more preferably up to a maximum of three, more preferably up to a maximum of two, in particular one, conservative amino acid substitutions. Examples of conservative substitutions include substitutions of one hydrophobic residue for another, such as F, V, L or A for one another, or substitutions of one polar residue for another, such as between K and R; E and D; or Q and N. Other such conservative substitutions, for example, substitutions of entire regions having similar hydrophobicity properties, are well known (Kyte and Doolittle, 1982, J. Mol. Biol. 157(1): 105-132). Exemplary amino acid substitutions are presented in the following Table:

| Original residues | Examples of substitutions |
| --- | --- |
| Arg (R) | His, Lys |
| Asn (N) | Gln |
| Asp (D) | Glu |
| Cys (C) | Ser |
| Gln (Q) | Asn |
| Glu (E) | Asp |
| Gly (G) | Pro, Ala |
| His (H) | Lys, Arg |
| Ile (I) | Leu, Val, Met, Ala, Phe |
| Leu (L) | Ile, Val, Met, Ala, Phe |
| Lys (K) | Arg, His |
| Met (M) | Leu, Ile, Phe |
| Phe (F) | Leu, Val, Ile, Tyr, Trp, Met |
| Pro (P) | Ala, Gly |
| Ser (S) | Thr |
| Thr (T) | Ser |
| Trp (W) | Tyr, Phe |
| Tyr (Y) | Trp, Phe |
| Val (V) | Ile, Met, Leu, Phe, Ala |

According to a preferred embodiment of the present invention the potency of the peptide can be modified by changing, deleting, inserting or adding amino acid residues to the peptide by, for instance, chemical peptide synthesis. Conservative exchange of amino acid residues at specific positions of the peptide are tolerated without affecting activity. Insertions of amino acids are also possible. An improvement or impairment of the activity of the peptide can be made by specific amino acid substitutions. For activity in the cellular transfection assay, the following amino acid changes can be made: insertion of W or A between F8 and C9 of peptide I24; F8 can be L, A3 can be V or L, F4 can be Y, Y5 can be F, A6 can be deleted, C1 can be S, C7 can be R. The core motif of the peptide of the present invention is preferably C1-$X_1$-$X_2$-$X_3$-$X_4$-(A)-C2-$X_5$-(WA)-C3 (SEQ ID No. 59) wherein $X_1$ is L or A, and $X_2$ being the aliphatic residues A, V or L and $X_3$ and $X_4$ being aromatic amino acid residues F or Y. Position C2 can be replaced by a different amino acid residue. In a particularly preferred embodiment of the present invention this motif represents the minimal motif to cause an inhibitory effect on gene expression from "foreign" DNA and inhibition of RNA polymerase activity.

"A" in formula (I) stands for alanine, "C" for cysteine, "S" for serine, "L" for leucine, "V" for valine, "F" for phenylalanine, "Y" for tyrosine, "R" arginine and "W" for tryptophan. "-" in formula (I) indicates a peptidic bond between two amino acid residues as occurring in peptides, polypeptides and proteins.

In a particularly preferred embodiment of the present invention $X_6$ of formula (I) is C.

In a further preferred embodiment of the present invention $X_1$ is C, $X_2$ is L and $X_6$ is C.

In another preferred embodiment of the present invention m is 1.

In a preferred embodiment of the present invention the peptide of the present invention comprises or consists of amino acid sequence $X_1$-$X_2$-$X_3$-$X_4$-$X_5$-(A)$_m$-C-$X_7$-(X$_8$)$_n$-C (SEQ ID No. 60), wherein $X_1$ is C or S, $X_2$ is L or A, $X_3$ is A, V or L, $X_4$ is F or Y, $X_5$ is Y or F, $X_7$ is F or L, $X_8$ is W or A and m and n are independently 0 or 1 or a variant thereof.

In another preferred embodiment of the present invention the peptide of the present invention comprises or consists of amino acid sequence C-L-$X_3$-$X_4$-$X_5$-(A)$_m$-C-$X_7$-(X$_8$)$_n$-C (SEQ ID No. 61), wherein $X_3$ is A, V or L, $X_4$ is F or Y, $X_5$ is Y or F, $X_7$ is F or L, $X_8$ is W or A and m and n are independently 0 or 1 or a variant thereof.

In order to enhance the capability of the compound of the present invention to inhibit or prevent translation and/or transcription of foreign nucleic acid molecules within an organism/cell said compound may comprise more than one peptide according to formula (I) and the present invention. Hence, the compound of the present invention may comprise or consist of 1 to 4, preferably 1 to 3, more preferably 1 or 2, peptides comprising or consisting of formula I.

The peptidic compound of the present invention may comprise more than one peptide of formula (I), whereby each peptide may consist of the same amino acid sequence or of different amino acid sequences. In a particularly preferred embodiment of the present invention the compound comprises two or more peptides of formula (I) and the present invention consisting of the same amino acid sequence. The resulting multimers (e.g. dimers and trimers) have the advantage that the transcription/translation inhibitory effect of the peptides of the present invention can be increased significantly.

According to a preferred embodiment of the present invention the peptide of the present invention consists of 8 to 40, preferably 8 to 30, more preferably 8 to 20, more preferably 8 to 15, more preferably 8 to 12, more preferably 8 to 10, amino acid residues.

The peptide of the present invention may be linear or cyclic. Methods for producing cyclic compounds, in particular cyclic peptides, are well known in the art. Due to the presence of cysteine residues at the C-terminal end and in some cases at the N-terminal end of the peptide of formula (I) and the present invention the production of cyclic peptides is facilitated. Of course, cyclic peptides can also be synthesized by providing an amide bond between the N- and C-terminal end of the peptide of the present invention.

According to a preferred embodiment of the present invention the amino acid sequence of the peptide of the present invention is selected from the group consisting of CLAFYACFWC (SEQ ID No. 2), CLAFYACLWC (SEQ ID No. 3), CLAFYACFAC (SEQ ID No. 4), CLVFYACFC (SEQ ID No. 5), CLAFYACFC (SEQ ID No. 6), CLLYFCFC (SEQ ID No. 7), CAAFYACFC (SEQ ID No. 8), SLAFYACFAC (SEQ ID No. 9), CLAFYARFC (SEQ ID No. 10), CLAFYCFAC (SEQ ID No. 11), CLAFYCFC (SEQ ID No. 12), and CLAYFCFC (SEQ ID No. 13).

Particularly preferred peptides of the present invention comprise or consist of an amino acid sequence selected from the group consisting of CLAFYACFWC (SEQ ID No. 2), CLAFYACLWC (SEQ ID No. 3), CLAFYACFAC (SEQ ID No. 4), CLVFYACFC (SEQ ID No. 5), CLAFYACFC (SEQ ID No. 6) and CLLYFCFC (SEQ ID No. 7), in particular CLAFYACFWC (SEQ ID No. 2) or CLAFYACLWC (SEQ ID No. 3).

In order to facilitate the translocation of the compound and peptides of the present invention into the cell or between cell compartments the compound of the present invention or the at least one peptide according to the present invention is modified to exhibit cell-penetrating properties. The presence of cell-penetrating moieties within the peptidic compound of the present invention allows to control more efficiently the translocation of said compound into cells and between cell compartments. This may result in an even better inhibition or prevention of translation and/or transcription of foreign nucleic acid molecules within a cell or organism because the compound and peptide of the present invention can be positioned within a cell or organism where said translation and/or transcription shall be inhibited or reduced.

According to a preferred embodiment of the present invention the at least one peptide or peptidic compound is fused C- and/or N-terminally directly or via a linker to at least one cell-penetrating peptide.

The term "cell-penetrating peptides", as used herein, refers to (short) peptides that are able to transport different types of molecules across plasma membrane, and, thus, facilitate cellular uptake of various molecular molecules (from nanosize particles to small chemical molecules, macromolecules and large fragments of DNA). The molecule to be transported is associated with the cell penetrating peptide either through chemical linkage via covalent bonds (e.g. conjugation, fusion) or by non-covalent interactions such as by Pep-1. Cell-penetrating peptides typically have an amino acid composition that either contains a high relative abundance of positively charged amino acids such as lysine or arginine or have a sequence that contains an alternating pattern of polar/charged amino acids and non-polar, hydrophobic amino acids. These two types of structures are referred to as polycationic or amphipathic, respectively. Cell-penetrating peptides are of different sizes, amino acid sequences and charges but all of these peptides have a common characteristic which is the ability to translocate the plasma membrane and facilitate the delivery of various molecules to the cytoplasm or to an organelle of a cell.

The peptide or peptidic compound of the present invention may be fused C- and/or N-terminally directly or via a linker to at least one cell-penetrating peptide. A linker has the advantage to provide a distance between the peptide and/or compound of the present invention and the cell-penetrating peptide. A further advantage is to incorporate one or more cleavage sites between the peptide and/or compound of the present invention and the cell-penetrating peptide allowing a protease, for instance, the removal of the cell-penetrating peptide.

According to another preferred embodiment of the present invention the cell-penetrating peptide is selected from the group consisting of a TAT peptide and a polycationic tag.

As mentioned above cell-penetrating peptides can have polycationic structures. Therefore, it is particularly preferred to add polycationic peptides (i.e. polycationic tags) to the peptide and/or compound of the present invention. Other cell-penetrating peptides can be derived from naturally occurring proteins which are known to support the translocation of other molecules through cell membranes. The TAT peptide, for instance, obtainable from the human immunodeficiency virus (HIV) is a well-known cell-penetrating peptide.

According to a preferred embodiment of the present invention the cell-penetrating peptide is derived from the TAT protein of the human immunodeficiency virus (HIV) and may comprise or consist of amino acid residues 37 to 72, more preferably of amino acid residues 37 to 60, more preferably amino acid residues 48 to 60, of SEQ ID No. 14 (MEPVDPRLEPWKHPGSQPKTACTT-CYCKKCCFHCQVCFTTKALGI-SYGRKKRRQRRRPPQGSQTHQVSL-SKQPTSQPRGDPTGPKE), in particular comprising or consisting of the amino acid sequence GRKKRRQRRRPPQ (SEQ ID No. 15), YGRKKRRQRRR (SEQ ID No. 16), CYGRKKRRQRRR (SEQ ID No. 17), YGRKKRRQRRRGGG (SEQ ID No. 18) or CGRKKRRQRRR (SEQ ID No. 19), wherein GRKKRRQRRRPPQ (SEQ ID No. 15) is most preferably used.

As mentioned above, another aspect of the present invention relates to peptide I24 or any other peptide of the present invention fused to a molecule which can enhance cell-permeability or cell-penetration. Such a tag can be, for instance, a TAT peptide or a polycationic tag, such as a polyarginine tag. Experiments have shown that the TAT-tag (TAT-I24: GRKKRRQRRRPPQCLAFYACFC; SEQ ID NO: 20), for instance, increases the potency of the peptide in inhibition of plasmid-encoded luciferase levels when transfected together with the plasmid-DNA (IC50=0.06 µM) while the TAT peptide alone is inactive.

Cell-penetrating peptides to be used in the present invention can be also derived from *Drosophila Antennapedia* protein homeodomain comprising the sequence RQIKIWFQNRRMKWKK (SEQ ID NO: 21), or polyarginine stretches including RRRRRRR (SEQ ID NO:22), i.e. (Arg)7 , RRRRRRRC (SEQ ID NO: 23),i.e. (ARG)7-C, or RRRRRRRR (SEQ ID NO: 24), i.e (ARG) 8, or RRRRRRRRR (SEQ ID NO: 25), i.e (ARG) 9, or may be derived from buforin comprising the sequence TRSSRAGLQFPVGRVHRLLRK (SEQ ID NO: 26), or may be derived from Transportan having the sequence GWTLNSAGYLLGKINLKALAALAKKIL (SEQ ID NO: 27) or may be selected from the KALA peptide comprising the sequence WEAKLAKALAKALAKHLAKALAKA-LKACEA (SEQ ID NO: 28), MAP comprising the sequence KLALKLALKALKAALKLA (SEQ ID NO: 29), or maybe selected from Pep-1 comprising the sequence KETWWETWWTEWSQPKKKRKV (SEQ ID NO: 30), hCT (9-32), comprising the sequence LGTYTQDFNKFHTFPQTAIGVGAP (SEQ ID NO: 31), pVEC, comprising the sequence LLIILRRRIRKQA-HAHSK (SEQ ID NO: 32), pISL, comprising the sequence RVIRVWFQNKRCKDKK (SEQ ID NO: 33); Erns, comprising the sequence RQGAARVTSWLGRQLRIAGKR-LEGRSK (SEQ ID NO: 34); Restriction L3, comprising the sequence KLIKGRTPIKFGR (SEQ ID NO: 35); orMPH comprising the sequence GALFLGFL-GAAGSTMGAWSQPKSKRKV (SEQ ID NO: 36) or GALFLGFLGAAGSTMGAWSQPKSKRKV-cysteamide; or derived from SV-40 Large T-antigen Nuclear Localization signal (NLS) comprising the sequence PKKKRKVEDPYC (SEQ ID NO: 37), or CGGGPKKKRKVED (SEQ ID NO: 38), or rabies Virus Glycoprotein (RVG) comprising the sequence YTIWMPENPRPGTPCDIFT-NSRGKRASNG (SEQ ID NO: 39).

Gene expression from an infecting virus, such as of baculovirus, can be reduced by the peptide fused to a cell-permeable tag as exemplified by reduced luciferase expression of a baculovirus encoding luciferase gene under control of the CMV promoter with I24 fused to an N-terminal TAT tag (TAT-I24: GRKKRRQRRRPPQCLAFY-ACFC; SEQ ID NO:20), while the untagged peptide I24 is only weakly active in inhibition of luciferase expression. The IC50 for inhibition of baculovirus-mediated luciferase expression by TAT-I24 is 0.15 µM. In one aspect, the invention relates to the fusion of peptide and tag which is superior over peptide or tag alone. In another aspect, the invention relates to the fusion of peptide and tag which can also reduce mRNA levels of the baculovirus-encoded gene while not inhibiting expression of cellular genes, exemplified by unaffected expression of interleukin-8 mRNA.

Another aspect of the present invention relates to the TAT-tagged peptide I24 which is—like all peptides and compounds of the present invention—able to inhibit gene expression by adenovirus, a double-stranded DNA virus, albeit inhibition occurs at higher concentrations (IC50=6 µM). In addition to inhibition of reporter gene expression, expression of the viral hexon gene is inhibited in a comparable manner.

According to a preferred embodiment of the present invention the TAT-tagged peptide I24 is able to inhibit viral replication in target cells, exemplified by reduction of adenovirus particles released to the supernatant and reduction of cell detachment compared to vehicle-treated cells after adenovirus infection, demonstrating inhibition of virus production in the target cell.

In another aspect, the present invention relates to the TAT-tagged peptide I24 which—like all peptides and compounds of the present invention—can inhibit gene expression and replication of vaccinia virus, a DNA virus belonging to the nucleocytoplasmic large DNA viruses of the family of Poxviridae. When HEK293 cells were infected with vaccinia virus and treated with TAT-I24, viral gene expression was inhibited by >95% and virus replication by >90% at 20 µM TAT-I24.

In another aspect, the present invention relates to the TAT-tagged peptide I24 which—like all peptides and compounds of the present invention—can inhibit gene expression and replication of herpes viruses, double-stranded DNA viruses, exemplified by inhibition of herpes simplex virus replication. Other members of family of Herpes viruses are cytomegalovirus or varicella zoster virus amongst others, such as Epstein-Barr virus.

In another aspect, the present invention relates to the TAT-tagged peptide I24 which—like all peptides and compounds of the present invention—can also cause inhibition of gene expression of an RNA virus. Partial inhibition of gene expression is seen by a single-stranded RNA virus, exemplified by Lentivirus-Luc, a retrovirus containing luciferase under control of a CMV promoter. When HEK293 cells were treated with peptide TAT-I24 and infected with Lentivirus encoding luciferase under control of the CMV promoter, a 75% reduction in luciferase levels was observed at the highest concentration (20 µM).

The inhibitor/peptide of the present invention, exemplified by peptide I24, consists of nine amino-acid residues with the following sequence (from the amino (N)-terminus to the carboxy (C)-terminus) Cys-Leu-Ala-Phe-TyrAla-Cys-Phe-Cys (SEQ ID NO: 6). Said peptide may contact the DNA molecule when transferred by any means to the target cell presumably at the cell membrane or within the cytosol. The peptide may already contact the DNA molecule before entering the cell or contacts the DNA molecule inside the cell, such as by a cell-penetrating version of the peptide.

The sequence of peptide I24 is derived from a peptide, which was originally identified by a phage screening against a translating ribosome to identify peptide binders of signal peptides and which is disclosed in the patent application WO 2011/086116 (LAFYACF (SEQ ID NO: 39 in WO 2011/086116)). However, the mode-of-action described herein is unrelated to the original signal peptide screening target. Testing of the peptide in various cellular systems showed an effect independent of the original signal peptide target. Surprisingly, the peptide inhibited gene expression from a "foreign" DNA brought into a target cell while not affecting cellular, genome-encoded gene expression. There is no relation between signal peptides and gene expression regulation from "foreign" DNA known in the art supporting the novelty of these findings.

According to a particularly preferred embodiment of the present invention the peptidic compound and/or the at least one peptide of the present invention is fused or conjugated to a label.

The peptide and/or compound of the present invention may be conjugated or fused to another molecule which acts as a label for the fusion or conjugation product. The presence of labels allows the direct or indirect detection and localisation of the peptide and/or compound of the present invention, for instance, in a cell or organism.

The label used within the present invention may have varying structures including polypeptides, proteins and other chemical structures. The label is preferably selected from the group consisting of a dye, preferably a fluorescent dye, more preferably a fluorescent protein, streptavidin, biotin, or a dye-binding peptide.

The peptide of the present invention can be also fused—preferentially via its N-terminal end—to other components such as other peptides or chemicals such as dyes or biotin which may be useful for localization and activity studies. The compound of the present invention, preferably comprising peptide I24, can be also a multimer, preferably a dimer. The dimer showed in the examples increased potency compared to the monomer (IC50=0.09 µM).

A further aspect of the present invention relates to a peptide or compound according to the present invention for the use in the treatment of a disorder or disease associated with the transcription and/or translation of heterologous nucleic acid molecules in cells of a mammal or human individual.

The peptides and compounds of the present invention can be used in the treatment of a disease or disorder which are caused by the translation and/or transcription of heterologous nucleic acid molecules in cells of mammals and human subjects. Such diseases and disorders include among others viral infections, such as infection by herpes simplex virus, causing herpes labialis and genital herpes, cytomegalovirus, varicella zoster virus causing chickenpox and shingles in adults, papillomavirus causing warts or certain types of cancer, or adenovirus.

A "disorder or disease associated with the transcription and/or translation of heterologous nucleic acid molecules in cells" includes disorders and diseases which are caused by the translation or transcription of nucleic acid molecules which are usually not present in cells which are considered to be healthy.

Another aspect of the present invention relates to a peptide or a peptidic compound of the present invention for the use in the treatment of a viral, bacterial, parasitic, or fungal infections in a mammal or human individual. The peptides or peptidic compounds of the present invention can be used in the treatment of infections by a DNA virus, such as a double-stranded DNA virus, preferably a virus of the family of Poxviridae, more preferably a virus of the family of Adenoviridae or most preferentially a virus of the family of Herpesviridae, in particular herpes simplex virus, cytomegalovirus and varicella zoster virus.

The peptides and peptidic compounds of the present invention have shown to be inhibiting or reducing significantly the transcription and/or translation rate of heterologous ("foreign") nucleic acid molecules being present in a cell or (multicellular) organism. The peptides and, thus, the compounds of the present invention having these properties result in the treatment of a viral, bacterial, parasitic or fungal infection in a mammal or human individual. In particular infections caused by viruses can be treated using the peptides and compounds of the present invention, because viruses usually require other organisms or cells to replicate themselves.

The peptides and compounds of the present invention can be administered to a mammal or human subject orally, intravenously, subcutaneously, topically, intravaginally, intraocular, inhaled or nasal.

The peptides and compounds as described herein of the invention can be administered orally, intravenously, subcutaneously, topically, intravaginally, intraocular, inhaled or nasal to a subject alone (e.g. as a purified peptide or compound) or as a component of a composition or medicament, as described herein. The compositions can be formulated with a physiologically acceptable carrier or excipient to prepare a pharmaceutical composition. The formulation should suit the mode of administration, for example intravenous or subcutaneous administration. Methods of formulating compositions are known in the art (see, e.g., Remington's Pharmaceuticals Sciences, 17th Edition, Mack Publishing Co., (Alfonso R. Gennaro, editor) (1989)).

Suitable pharmaceutically acceptable carriers include water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, liposomes, viscous paraffin, perfume oil, fatty acid esters, hydroxymethylcellulose, polyvinyl pyrolidone, etc., as well as combinations thereof. The formulations can be mixed with auxiliary agents (e.g., lubricants, preservatives, stabilizers, wetting agents, emulsifiers, salts for influencing osmotic pressure, buffers, coloring and/or aromatic substances and the like) which do not deleteriously react with the peptides and compounds of the present invention or interfere with their activity. In a preferred embodiment, a water-soluble carrier suitable for intravenous administration is used.

The formulation of the present invention comprising the peptides and compounds described herein can also contain wetting or emulsifying agents or pH buffering agents. The composition can be a liquid solution, suspension, emulsion, sustained release formulation or powder. The composition can also be formulated as a suppository, with traditional binders and carriers such as triglycerides.

In a preferred embodiment of the present invention a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The peptides and compounds of the present invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The peptide and peptidic compound of the present invention can be administered by any appropriate route, preferably topical, nasal, subcutaneously, intravenously, by inhalation, parenterally, intradermally, transdermally, rectally, intravaginally, intraocular or transmucosally. More than one route can be used concurrently, if desired.

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100%. Alternatively or additionally, in some embodiments, an appropriate dose or amount is determined through use of one or more in vitro or in vivo assays to help identify desirable or optimal dosage ranges or amounts to be administered.

The peptide and compound of the present invention is administered preferably at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the mammal or human individual (e.g. treating, modulating, curing, preventing and/or ameliorating the underlying disease or disorder). Appropriate doses or amounts to be administered may be extrapolated from dose-response curves derived from in vitro or animal model test systems.

Therapeutically effective dosage amounts of the peptides and compounds of the present invention including salts thereof may range from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). According to a preferred embodiment of the present invention the peptide and compound of the present invention is administered in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg and/or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

The peptide and compound of the present invention may be administered in one or more doses. The therapeutically effective amount of the peptide and/or compound of the present invention may be administered in one or more days, most preferably in one day.

A therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. The therapeutically effective amount described herein may be provided in one dose per day.

A therapeutically effective dosage amount may be, for example, about 0.001 mg/kg weight to about 1 mg/kg weight, e.g. from about 0.001 mg/kg weight to about 0.9 mg/kg weight, from about 0.001 mg/kg weight to about 0.8 mg/kg weight, from about 0.001 mg/kg weight to about 0.8 mg/kg weight, from about 0.001 mg/kg weight to about 0.7 mg/kg weight, from about 0.001 mg/kg weight to about 0.6 mg/kg weight, from about 0.001 mg/kg weight to about 0.5 mg/kg weight, from about 0.01 mg/kg weight to about 1 mg/kg weight, from about 0.01 mg/kg weight to about 0.9 mg/kg weight, from about 0.01 mg/kg weight to about 0.8 mg/kg weight, from about 0.01 mg/kg weight to about 0.7 mg/kg weight, from about 0.01 mg/kg weight to about 0.6 mg/kg weight, from about 0.01 mg/kg weight to about 0.5 mg/kg weight, from about 0.02 mg/kg weight to about 1 mg/kg weight, from about 0.02 mg/kg weight to about 0.9 mg/kg weight, from about 0.02 mg/kg weight to about 0.8 mg/kg weight, from about 0.02 mg/kg weight to about 0.7 mg/kg weight, from about 0.02 mg/kg weight to about 0.6 mg/kg weight, from about 0.02 mg/kg weight to about 0.5 mg/kg weight, from about 0.03 mg/kg weight to about 1 mg/kg weight, from about 0.03 mg/kg weight to about 0.9 mg/kg weight, from about 0.03 mg/kg weight to about 0.8 mg/kg weight, from about 0.03 mg/kg weight to about 0.7 mg/kg weight, from about 0.03 mg/kg weight to about 0.6 mg/kg weight, from about 0.03 mg/kg weight to about 0.5 mg/kg weight, from about 0.04 mg/kg weight to about 1 mg/kg weight, from about 0.04 mg/kg weight to about 0.9 mg/kg weight, from about 0.04 mg/kg weight to about 0.8 mg/kg weight, from about 0.04 mg/kg weight to about 0.7 mg/kg weight, from about 0.04 mg/kg weight to about 0.6 mg/kg weight, from about 0.04 mg/kg weight to about 0.5 mg/kg weight, from about 0.05 mg/kg weight to about 1 mg/kg weight, from about 0.05 mg/kg weight to about 0.9 mg/kg weight, from about 0.05 mg/kg weight to about 0.8 mg/kg weight, from about 0.05 mg/kg weight to about 0.7 mg/kg weight, from about 0.05 mg/kg weight to about 0.6 mg/kg weight, from about 0.05 mg/kg weight to about 0.5 mg/kg weight.

A therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular subject can be varied (e.g., increased or decreased) over time, depending on the needs of said subject (i.e. mammal or human individual).

The peptides and compounds of the present invention may be administered at an effective dose ranging from about 1-1,000 µg/kg/day (e.g., ranging from about 1-900 µg/kg/day, 1-800 µg/kg/day, 1-700 µg/kg/day, 1-600 µg/kg/day, 1-500 µg/kg/day, 1-400 µg/kg/day, 1-300 µg/kg/day, 1-200 µg/kg/day, 1-100 µg/kg/day, 1-90 µg/kg/day, 1-80 µg/kg/day, 1-70 µg/kg/day, 1-60 µg/kg/day, 1-50 µg/kg/day, 1-40 µg/kg/day, 1-30 µg/kg/day, 1-20 µg/kg/day, 1-10 µg/kg/day). In some embodiments, the peptides and compounds of the present invention are administered at an effective dose ranging from about 1-500 µg/kg/day. In some embodiments, the peptides and compounds of the present invention are administered at an effective dose ranging from about 1-100 µg/kg/day. In some embodiments, the peptides and compounds of the present invention are administered at an effective dose ranging from about 1-60 µg/kg/day. In some embodiments, the peptides and compounds of the present invention are administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 ug/kg/day.

The peptides and compounds of the present invention may be administered via continuous infusion, preferably continuous intravenous infusion. The peptides and compounds of the present invention may be administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

Another aspect of the present invention relates to a nucleic acid molecule encoding a peptide or a compound according to the present invention.

The nucleic acid molecule of the present invention is a DNA or RNA molecule. Said nucleic acid molecule can be part of a vector, preferably a cloning or expression vector, which are well known in the art.

Another aspect of the present invention relates to the use of a peptide or compound according to the present invention for inhibiting transcription and/or translation of a heterologous nucleic acid molecule in a cell, preferably eukaryotic cell, more preferably mammalian or human cell, or an organism (e.g. mammal or human subject).

According to a preferred embodiment of the present invention the heterologous nucleic acid molecule is of viral, bacterial, parasitic or fungal origin.

According to a further embodiment of the present invention the heterologous nucleic acid molecule contains nucleic acid stretches encoding antibiotic resistance genes or functional fragments thereof.

The peptides and compounds of the present invention are also able to inhibit the transcription and/or translation of nucleic acid molecules encoding antibiotic resistance genes and thus to prevent or significantly reduce antibiotic resistance of microorganisms like bacteria. This is particularly advantageous because the peptides and compounds of the present invention allow to make bacteria susceptible to antibiotics although they are able to produce proteins which are responsible for antibiotic resistance. Therefore, the peptides and compounds of the present invention can be used for combatting antibiotic resistance bacteria.

A plasmid DNA, for instance an antibiotic-resistance gene containing DNA (e.g. a R-plasmid), can be transferred between bacteria by horizontal gene transfer. A plasmid can be either replicated outside the bacterial genome or can be integrated into the bacterial genome. Bacteria can become resistant to antibiotics when taking up such a DNA. In addition, virulence genes can be also transferred between bacteria. Management of bacterial infection will be a major challenge in future due to the world-wide development of antibiotic resistance in bacteria and lack of suitable drug candidates. An inhibitor of gene transfer between bacteria could have potential implications for medical treatment or hygiene measures in areas, e.g. hospitals, where resistance formation occurs. Inhibition of transfer of a "foreign" DNA molecule and inhibition of protein production by the inhibitor molecule could be therefore useful for therapeutic intervention in infectious diseases or for preventing of spread and formation of antibiotic-resistant bacteria.

Hence, another aspect of the present invention relates to the use of a peptide or compound according to the present invention for preventing bacterial cells to gain genes or functional fragments thereof capable to provide antibiotic resistance to said bacterial cells.

According to a preferred embodiment of the present invention the peptides and compounds of the present invention, in particular peptide I24, inhibit colony-formation on antibiotic-containing agar plates of *Escherichia coli* bacteria transformed with a plasmid containing the antibiotic resistance gene and peptide I24 simultaneously. The peptide is inactive when applied after transformation is completed. The inhibition by the peptide is independent of the antibiotic resistance gene used exemplified by reduced colony formation of *Escherichia coli* bacteria transformed with ampicillin- or kanamycin-resistance gene containing plasmids and growth on ampicillin- or kanamycin-containing agar plates.

It was further found that the peptides and compounds of the present invention, in particular peptide I24, inhibits plasmid replication and RNA production of the antibiotic-resistance gene exemplified by reduction of β-lactamase mRNA expression in *Escherichia coli* bacteria transformed with a plasmid containing the antibiotic resistance and peptide simultaneously.

The peptides and compounds of the present invention can inhibit or significantly reduce the transcription and/or translation of viral nucleic acid molecules. Hence, these peptides and compounds can be used as an additive for vaccines comprising attenuated viruses or administered together with attenuated viruses either to increase the safety of live vaccines or to indirectly attenuate the live vaccine.

Therefore, another aspect of the present invention relates to the use of a peptide or compound according to the present invention as an additive for an attenuated live vaccine. In an alternative aspect of the present invention the peptide and/or compound of the present invention may be co-administered with a live vaccine.

The peptide and compound of the present invention can be used to inhibit the transcription and/or translation of viral nucleic acid molecules in cells in order to reduce the viral titer within organisms (e.g. mammals and human individuals). This property can also be used to inhibit or prevent viral spread in cell cultures.

Hence, another aspect of the present invention relates to the use of a peptide or compound according to present invention to inhibit or prevent viral spread in cell cultures.

Another aspect of the present invention relates to the use of a compound according to the present invention to inhibit phage infection of bacteria.

Another potential application of the compound/inhibitor of the present invention is the prevention of phage infections in bacteria. A phage infection of bacterial cultures can be a problem particular in biotechnological applications including large-scale fermentations. Due to the capability of the compound of the present invention to inhibit the translation and/or transcription of foreign nucleic acid molecules within an organism/cell the replication of phages within bacteria can be inhibited or even prevented. This means that during the cultivation of bacterial cells the compound of the present invention or a composition comprising said compound is added to the culture medium.

Thus, another potential application of said inhibitor is prevention of phage infections in bacteria. A phage infection of bacterial cultures can be a problem particular in biotechnological applications including large-scale fermentations. Additionally, prevention of virus infections in animal cell culture may be another application of biotechnological and biopharmaceutical relevance. The inhibitor may also be expressed intracellularly in a target cell and could be useful for biotechnological applications such as prevention of viral or phage infections or could be useful for control of gene expression.

The compound of the present invention may be labelled with other substances in order to allow its detection and/or visualisation. This may be helpful in the localisation of the compounds of the present invention in cells, tissue and organisms where the compounds inhibit the transcription and/or translation of heterologous/foreign nucleic acid molecules. Therefore, another aspect of the present invention relates to the use of a compound according to the present invention to localize the transcription and/or translation of a heterologous nucleic acid molecule within a eukaryotic cell.

According to a preferred embodiment of the present invention the heterologous/foreign nucleic acid molecule to be localized is of viral, bacterial, parasitic or fungal origin.

In one aspect, the present invention relates to the peptides and compounds of the present invention, preferably peptide I24, which reduces expression of a plasmid-encoded protein in eukaryotic cells when contacting the expression plasmid during transfection of the expression plasmid. The transfection of the plasmid-DNA can be performed for example by using a liposomal reagent, cationic polyamidoamine polymers, electroporation, calcium phosphate or DEAE-dextran.

The peptides and compounds of the present invention, preferably peptide I24, is able to reduce levels of a cytosolic protein in cell lysates exemplified by the reduction of luciferase levels from cells transfected with a luciferase-encoding expression plasmid and peptide simultaneously.

The peptides and compounds of the present invention, preferably peptide I24, are able to reduce the levels of a secretory protein in cell supernatants exemplified by the reduction of secreted alkaline phosphatase levels from cells transfected with a secreted alkaline phosphatase-encoding expression plasmid and peptide simultaneously.

In another aspect, the invention provides the peptides and compounds of the present invention, preferably peptide I24, which can also reduce levels of a nuclear protein in cell lysates exemplified by inhibition of the levels of a truncated version of NF-κB p65 (NF-κB p65 M2) when transfected with a NF-κB p65 M2 expression-plasmid and test peptide simultaneously.

The peptides and compounds of the present invention, preferably peptide I24, are able to reduce the levels of green fluorescence protein (GFP) in cell lysates when eukaryotic cells are simultaneously transfected with a GFP expression plasmid and peptide as determined by Western blot analysis. It was found that the peptides and compounds of the present invention reduce the overall number of GFP-positive cells in cells transfected with a GFP plasmid and peptide simultaneously.

Inhibition of protein production in expression plasmid-transfected eukaryotic cells by the peptides and compounds of the present invention, preferably peptide I24, is independent of the state of DNA (e.g. circular, supercoiled or relaxed DNA, linear DNA, circular plasmid-DNA, linearized plasmid-DNA, a PCR product and a double-stranded oligonucleotide). The peptide inhibits protein production in eukaryotic cells when transfected with a linear double-stranded DNA, such as a linearized plasmid or a double-stranded DNA fragment obtained by polymerase chain reaction (PCR).

In another aspect, the invention provides the peptides and compounds of the present invention, preferably peptide I24, inhibiting the protein production from expression plasmid-transfected eukaryotic cells in a dose-dependent manner with IC50 (half maximal inhibitory concentration) being between 0.1 to 2 μM, preferably 0.3 to 0.7 μM. The peptides and compounds of the present invention are active when they contact the DNA during transfection of eukaryotic cells but not when the peptide is added after the transfection procedure is completed.

Another aspect of the present invention relates to the cell-type independent effects of the peptide. The peptide I24 inhibits plasmid-encoded protein production when transfected together with the plasmid in various cell lines exemplified by the use of HEK293, CV-1, COS-7, MCF-7 or HT-29 cells.

The present invention is further illustrated by the following examples, however, without being restricted thereto.

EXAMPLES

Example 1: Sequence of Peptide I24

I24 is a peptide consisting of the nine amino-acid residues Cys-Leu-Ala-Phe-Tyr-Ala-Cys-Phe-Cys (CLAFYACFC, SEQ ID NO: 6). The peptide can be either linear or cyclized via cysteine residues and disulfide bonds.

Example 2: I24 Inhibits Expression-Vector Encoded Protein Production in Transiently Transfected Mammalian Cells HEK293 cells (human embryonic kidney cells) were transfected with a luciferase construct (luciferase coding region cloned into a eukaryotic expression plasmid under control of a CMV promoter) using Superfect (Qiagen) in the presence of DMSO as vehicle control or different doses of peptide I24. After 24 hrs, luciferase levels were analysed from cell lysates using a luciferase substrate. The peptide caused dose-dependent inhibition of luciferase production compared to vehicle control (FIG. 1a). HEK293 cells were transfected with secreted alkaline phosphatase (SEAP) cloned into a eukaryotic expression vector under control of a CMV promoter in the presence of DMSO or different doses of peptide I24. After 24 hrs, SEAP released to the supernatant was analysed by a colorimetric assay. I24 reduced production of SEAP in a dose-dependent manner in transfected HEK293 cells compared to vehicle control (FIG. 1b). The peptides J9 (cyclized version of I24 M23; CPSALAFYC (SEQ ID NO: 53)) and I21 (CSLTGPIAC (SEQ ID NO: 56)) served as inactive controls. HEK293 cells were transfected with an expression plasmid encoding a truncated version of NF-κB p65 (p65 M2) for 24 hrs. The production of p65 was analysed by Western blot from lysates of transfected cells (FIG. 1c). In cells transfected with p65 M2 and peptide I24 (20 μM), no p65 M2 could be detected by Western blot. HEK293 cells were transfected with an expression plasmid, encoding green fluorescence protein (GFP) in the presence and absence of peptide I24 (2 μM). Western blot analysis showed that GFP production and number of GFP-positive cells is reduced by peptide I24 (FIG. 1d, e).

Figure 2:
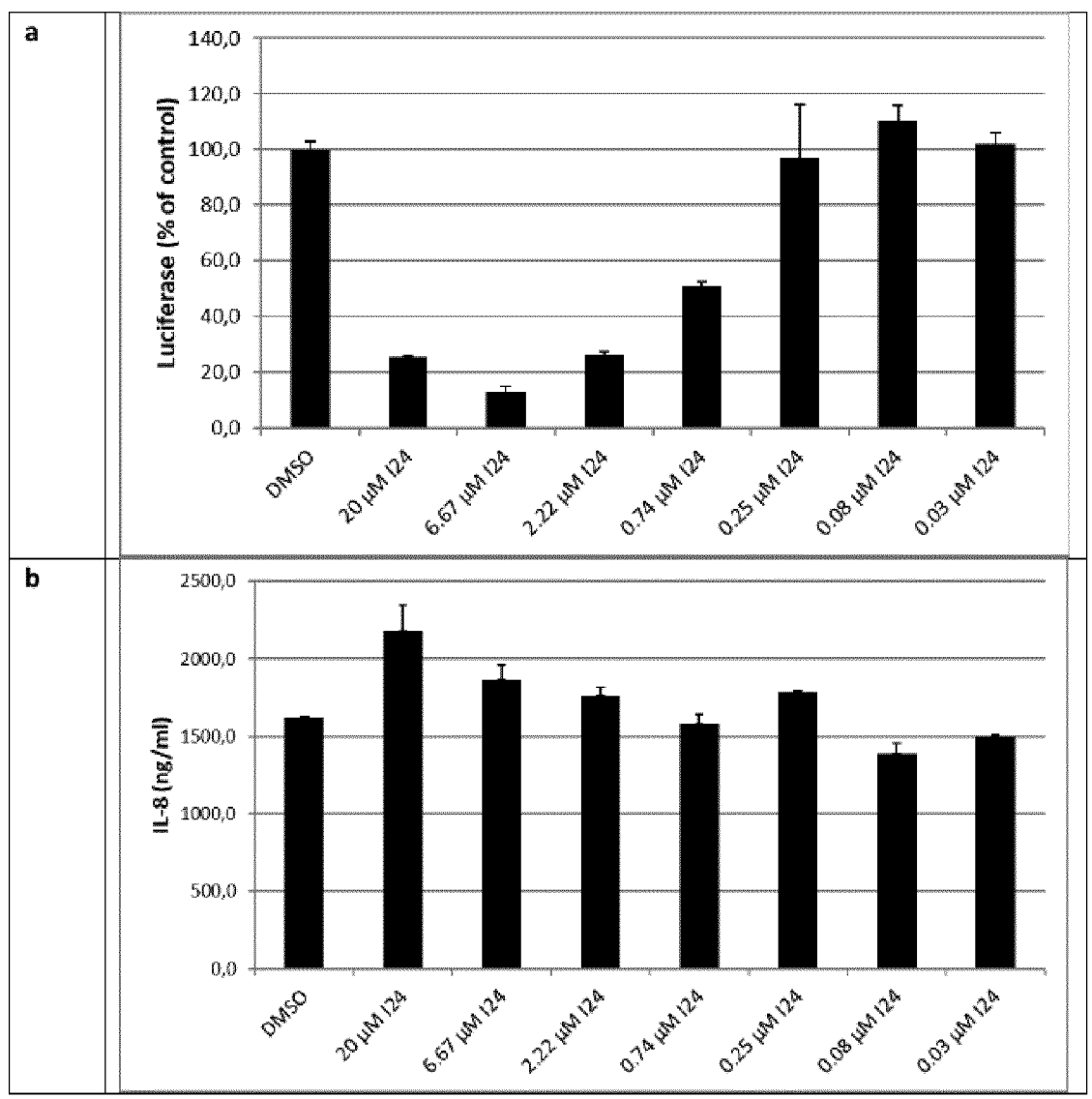
FIG. 2. The peptide I24 inhibits expression of luciferase when transfected with a plasmid driving luciferase under control of a truncated IL-8 promoter (a) while not inhibiting release of IL-8 (b).

Example 3: The Peptide I24 Inhibits Plasmid-Vector Encoded Gene Expression Under Control of a Truncated Interleukin-8 Promoter while not Inhibiting Expression of Endogenous Interleukin-8 in Transiently Transfected Cells HEK293 cells were transiently transfected with a construct containing the luciferase coding region under control of the truncated interleukin-8 (IL-8) promoter and peptide I24 and stimulated with tumor necrosis factor (TNF)-α 6 hrs after transfection and analysed 24 hrs post-transfection for expression of luciferase in cell lysates and released IL-8 in the supernatants by ELISA. The peptide reduced TNF-α-induced luciferase expression while release of IL-8 was not affected (FIG. 2).

Figure 3:
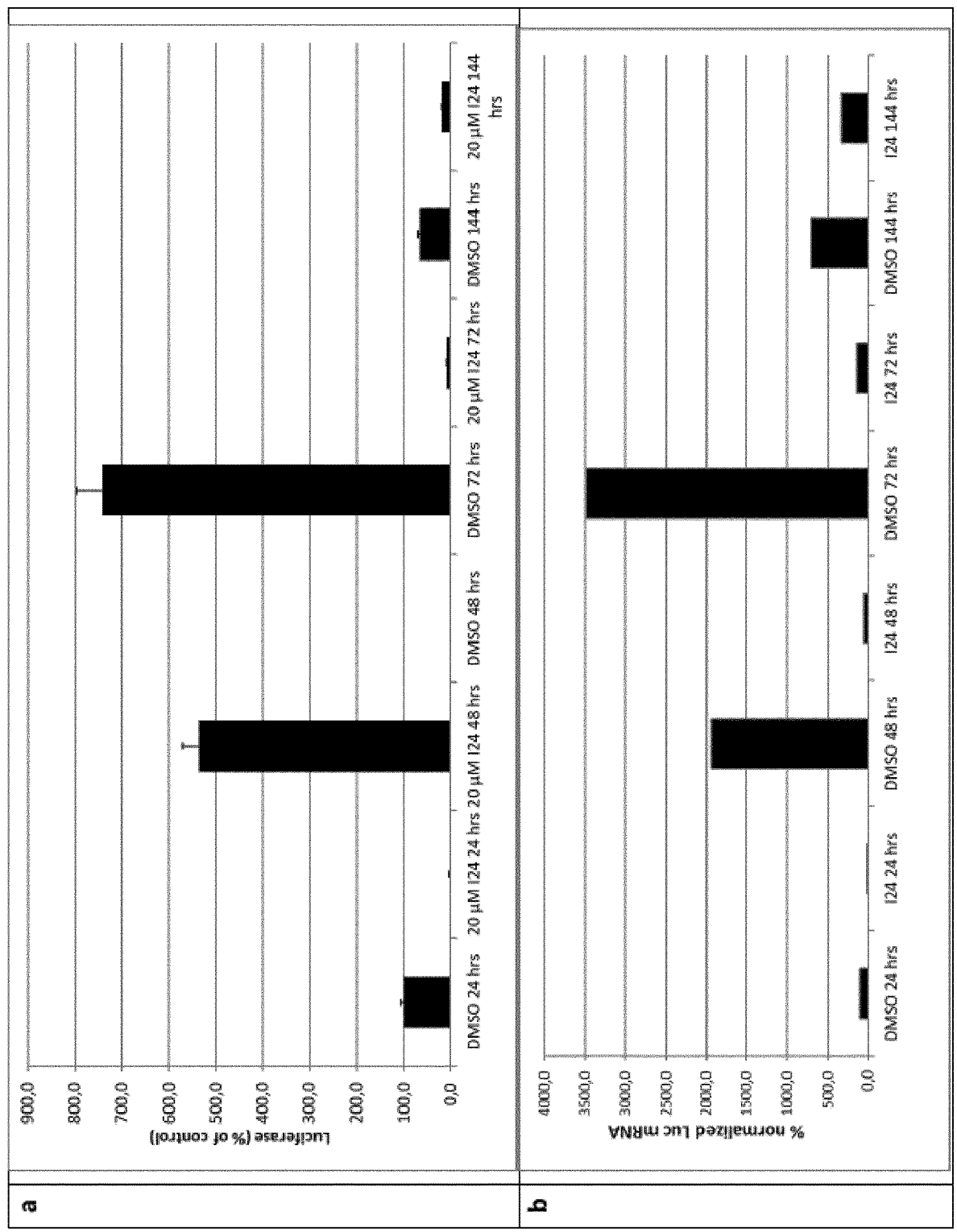
FIG. 3. Levels of luciferase protein (a) and mRNA (b) analysed after indicated time points after transfection of plasmid with peptide I24.

Example 4: Protein and Messenger RNA Levels are Down-Regulated when Peptide I24 is Transfected into Cells with the Expression Plasmid COS-7 African green monkey kidney cells were transfected with an expression plasmid driving luciferase under control of the CMV promoter and luciferase determined in cell lysates. For analysis of expression of luciferase mRNA, total RNA was isolated, treated with DNAse I and subjected to reverse transcription using random hexamers. Real-time PCR was performed with hydrolysis probes detecting luciferase and normalized to 18S rRNA transcript levels. Both, luciferase protein and mRNA levels were downregulated after different incubation times (FIG. 3).

Figure 4:
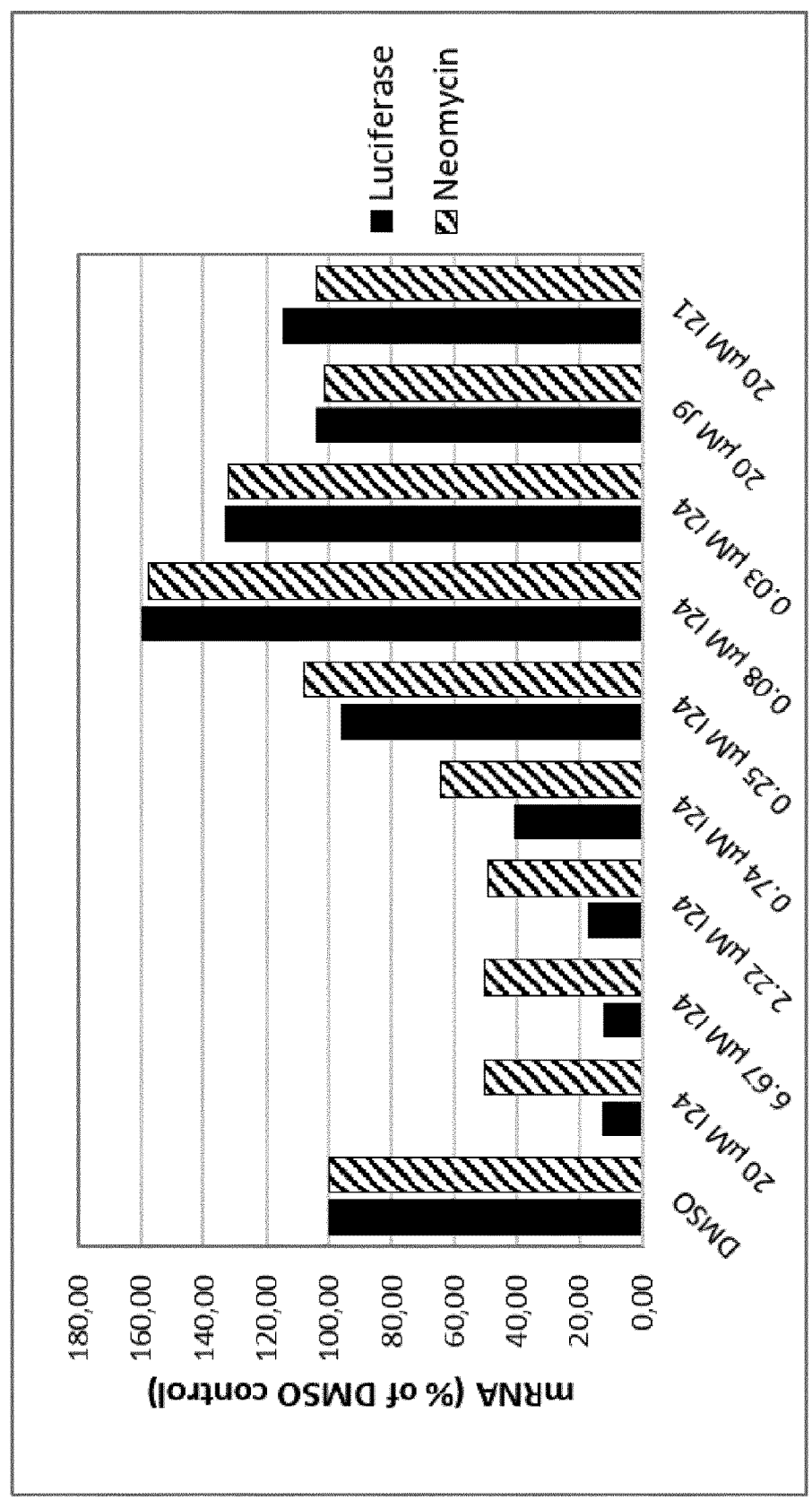
FIG. 4. The peptide I24 inhibits levels of mRNA of luciferase under control of the CMV promoter more effectively compared to mRNA levels of the neomycin resistance gene under control of the early SV40 promoter when transfected with a plasmid containing both genes on the same plasmid.

Example 5: Inhibition of Plasmid-Vector Encoded Gene Expression is Partially Dependent on the Promoter in Transiently Transfected HEK293 Cells HEK293 cells were transiently transfected in the presence of increasing concentrations of peptide I24 with an expression plasmid containing luciferase under control of the CMV promoter and the neomycin resistance gene under control of the early SV40 promoter. After 24 hrs, total RNA was isolated from the cells, digested with DNAse I to remove plasmid-DNA and subjected to reverse transcription. Quantitative real-time PCR analysis of luciferase and neomycin mRNA was performed using hydrolysis probes and normalized against GAPDH transcripts. While luciferase transcripts were reduced in the presence of increasing concentration of peptide I24 by 87%, neomycin mRNA levels were only reduced by about 50% (FIG. 4).

Figure 5:
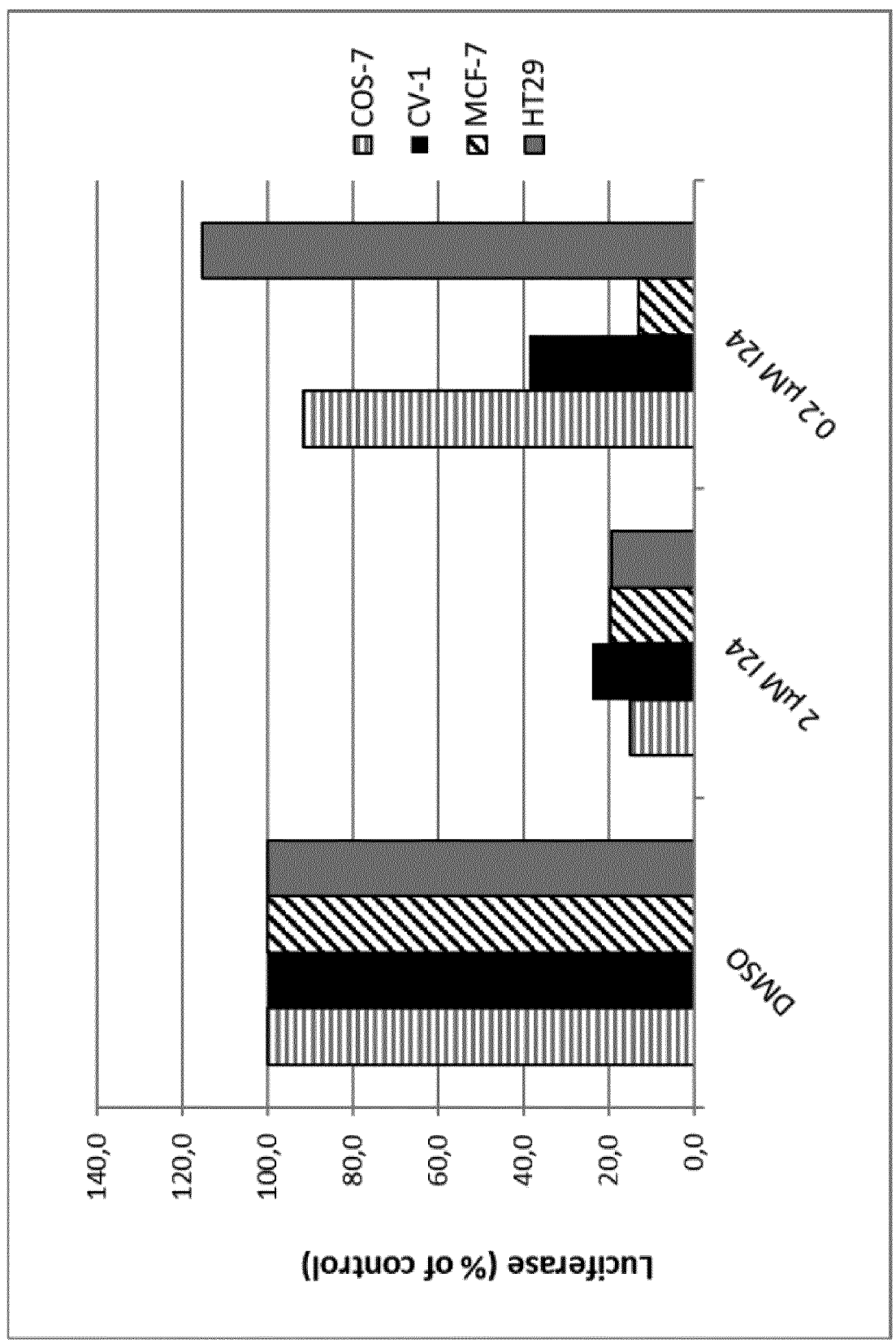
FIG. 5. The peptide I24 inhibits plasmid-encoded luciferase levels in different cell lines.

Example 6: Inhibition of Plasmid-Vector Encoded Gene Expression is Independent of the Cell Line Used The cell lines African Green Monkey kidney cells CV-1 and COS-7, as well as the human breast cancer cell line MCF-7 and the human colon cancer cell lines HT-29 were transiently transfected with a plasmid containing luciferase under control of a CMV promoter and different concentrations of peptide I24. Inhibition of the reporter gene luciferase was observed with all cell lines used (FIG. 5).

Example 7: A Cell Penetrating Version of I24 by Addition of an Amino-Terminal TAT-Tag or Dimerization Increases Potency of the Peptide I24

Figure 6:
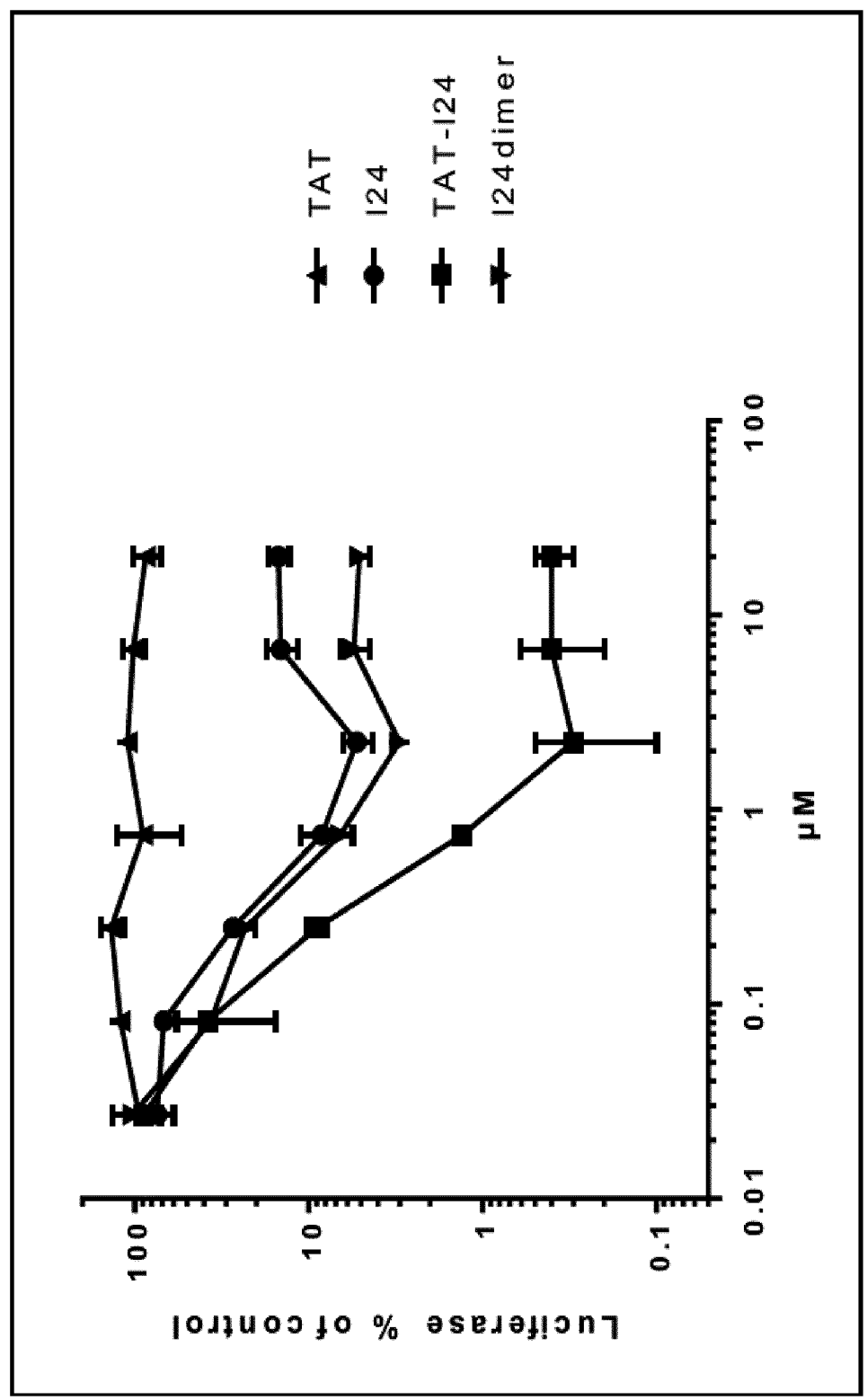
FIG. 6. Levels of luciferase protein after transient transfection of a luciferase-encoding plasmid and different concentrations of peptides I24, TAT, TAT-I24 and I24-dimer (for better resolution, both axes are shown in log-scale).

A cell-penetrating version of I24 by addition of an N-terminal TAT-tag was generated as was a dimer of I24 with two monomers separated by three glycine residues. Transient transfection with the peptides and a luciferase-encoding expression plasmid showed more potent inhibition of luciferase expression by TAT-I24. The I24-dimer was also more potent compared to peptide I24 but less potent compared to TAT-I24. The peptide representing the TAT tag alone (TAT) was inactive in inhibition of luciferase (FIG. 6).

Figure 7:
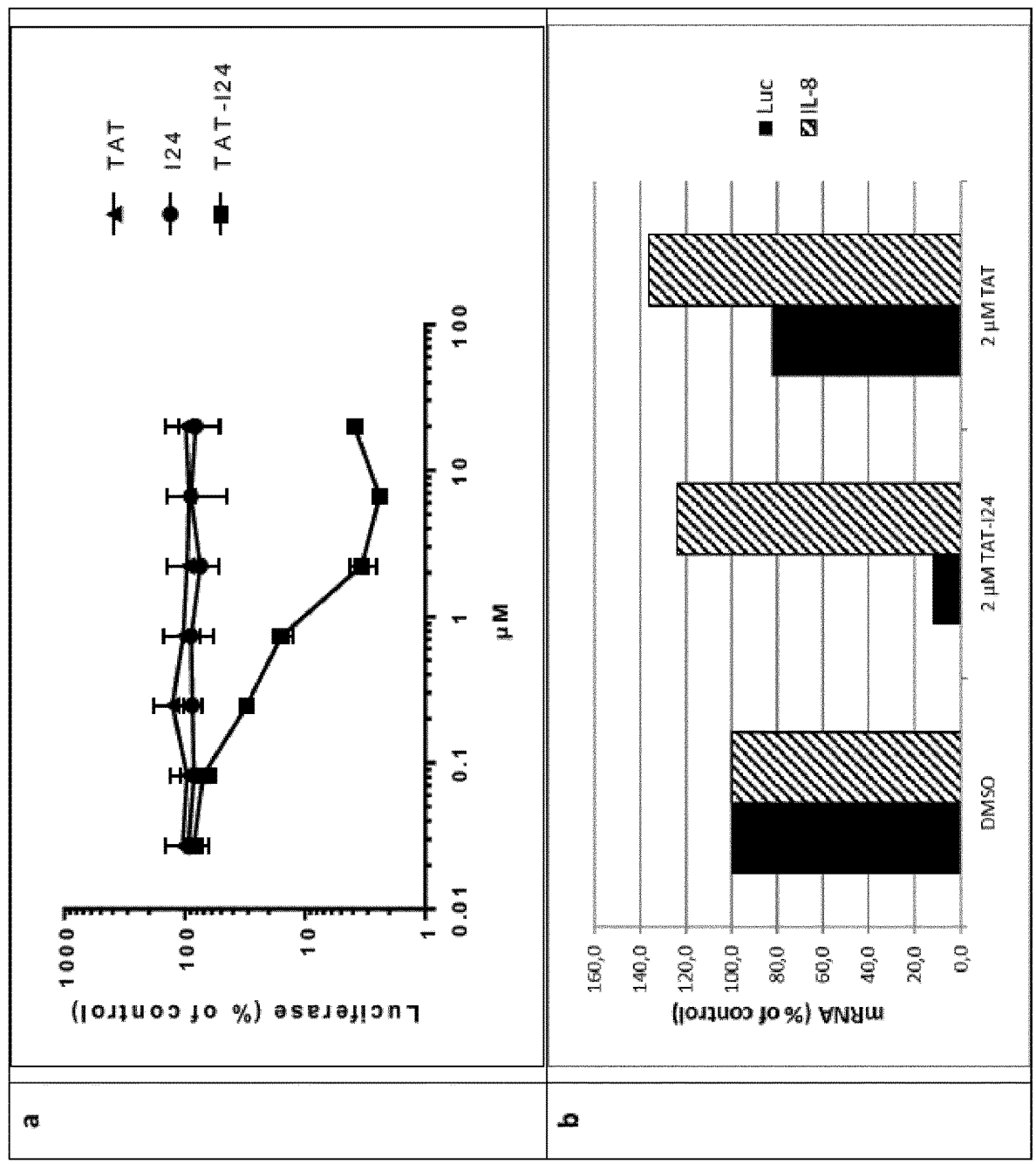
FIG. 7. (a) Inhibition of baculovirus-transduced luciferase gene expression in HEK293 cells treated with fusion peptide TAT-I24 (for better resolution both axes are shown in log-scale), and (b) mRNA levels of luciferase and IL-8 in cells treated with vehicle DMSO, fusion peptide TAT-I24 or TAT alone and baculovirus expressing luciferase and stimulation with TNF-α (b).

Example 8: Inhibition of Baculovirus-Mediated Gene Expression in HEK293 Cells with a Cell-Permeable Version of the Peptide I24 Fused to an Amino-Terminal TAT-Tag A baculovirus was generated with the luciferase coding region under control of the CMV promoter integrated in its viral genome. The baculovirus was applied to HEK293 cells pretreated for 10 minutes with DMSO or increasing concentrations of peptide I24, TAT and the fusion peptide TAT-I24. Luciferase expression is reduced in cells treated with cell-permeable fusion peptide TAT-I24 in a dose-dependent manner (FIG. 7a). Baculovirus-infected cells incubated with DMSO, TAT-I24 or TAT were stimulated with TNF-α and total RNA isolated from cells. After treatment of the RNA with DNAse I, reverse transcription was performed. Luciferase and IL-8 mRNA were analysed by real-time PCR. While luciferase mRNA is down-regulated by TAT-I24, mRNA levels of IL-8 remained unaffected by the treatment (FIG. 7b).

Figure 8:
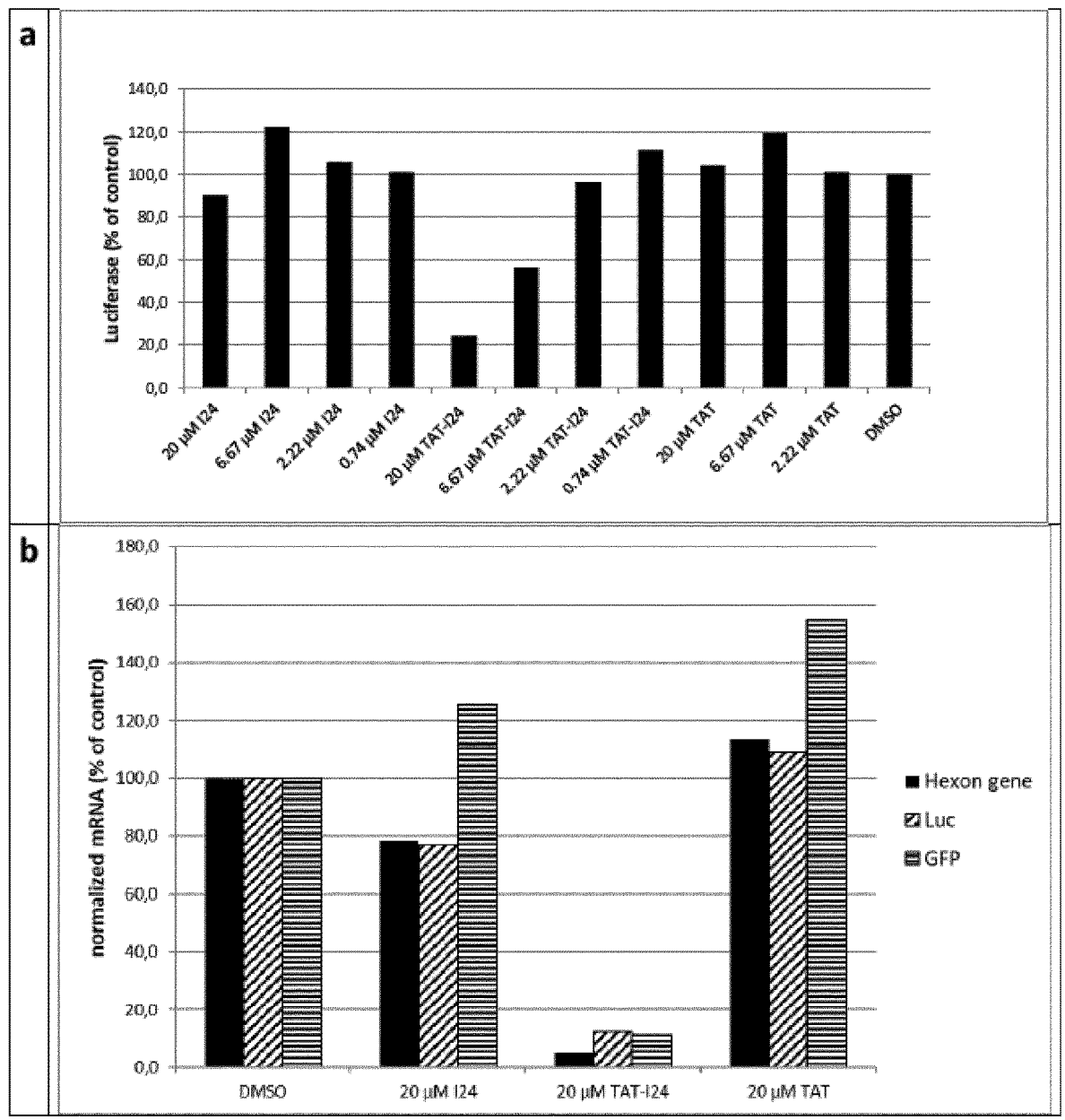
FIG. 8. TAT-I24 inhibits luciferase expression from HEK293 cells infected with adenovirus particles encoding luciferase and GFP (a). TAT-I24 inhibits mRNA levels of luciferase, GFP and adenovirus-encoded hexon gene (b). TAT-I24 inhibits formation and release of adenovirus particles to supernatants by infected cells (c). TAT-I24 inhibits cell detachment 96 hrs after adenovirus infection (d).
Figure 8:
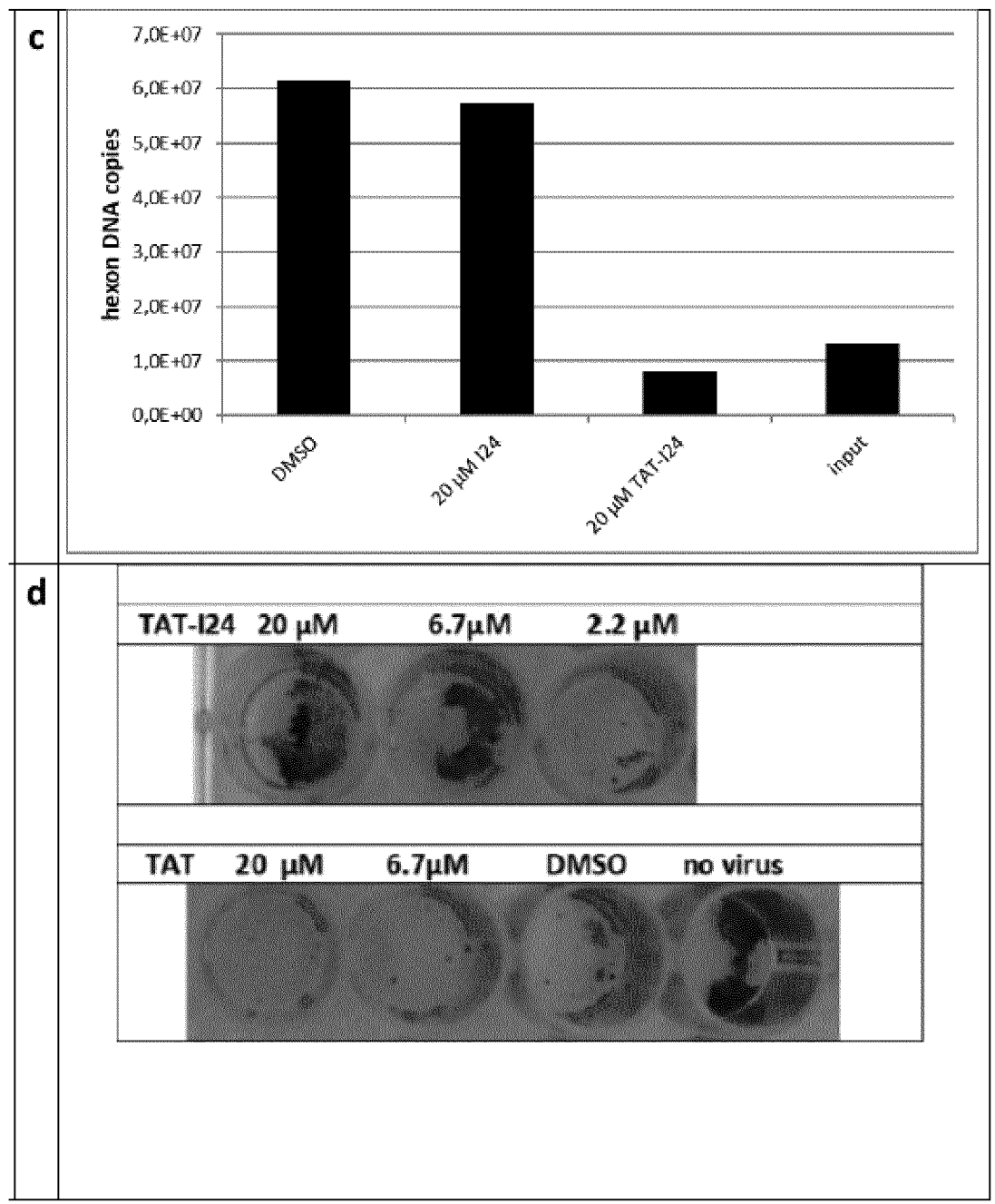

Example 9: The Cell-Permeable Peptide I24 Inhibits Gene Expression by Adenovirus and Inhibits Virus Replication in HEK293 Cells HEK293 cells were treated with increasing concentrations of the peptides I24, TAT-I24 or TAT alone and incubated with adenovirus encoding luciferase and green fluorescence protein (GFP) under control of the CMV promoter. Luciferase protein levels were downregulated by TAT-I24 with an IC50 of 6 µM (FIG. 8a). HEK293 cells were treated with vehicle control, the peptide I24, TAT-I24 or TAT alone (20 µM) and adenovirus particles encoding luciferase and GFP. After 72 hrs, RNA was isolated and luciferase and GFP as well as adenovirus hexon transcript levels analysed by real-time PCR and normalized to GAPDH. TAT-I24 caused inhibition of all three adenovirus-encoded genes (FIG. 8b). DNA was isolated from supernatants and adenovirus hexon DNA quantified using real-time PCR (FIG. 8c). TAT-I24 causes inhibition of cell detachment of virus-infected HEK293 cells determined by fixation and crystal violet staining 96 hrs after infection (FIG. 8d).

Example 10: The Cell-Permeable Peptide TAT-I24 Inhibits Gene Expression and Replication of Vaccinia Virus in HEK293 Cells HEK293T cells were treated with DMSO, TAT-I24 or TAT for 4 hrs before infection with vaccinia virus. Twenty-four hrs after infection, total RNA was isolated and treated with DNAse I before cDNA synthesis. Expression of transcripts of DNA-dependent RNA polymerase subunit rpo22, a vaccinia-virus encoded gene, was analysed by real-time PCR using SYBR Green and normalized to GAPDH mRNA levels. TAT-I24 dose-dependently inhibited rpo22 mRNA levels, while TAT alone caused no inhibition (a). Viral DNA was extracted from supernatants 24 hrs after infection and subjected to real-time PCR. Supernatants were subjected to a plaque assay using BSC-40 cells. At a concentration of 20 µM, TAT-I24 reduced amount of viral DNA (b) and number of plaque forming units (PFU) in the supernatants by >90% (c).

Figure 9:
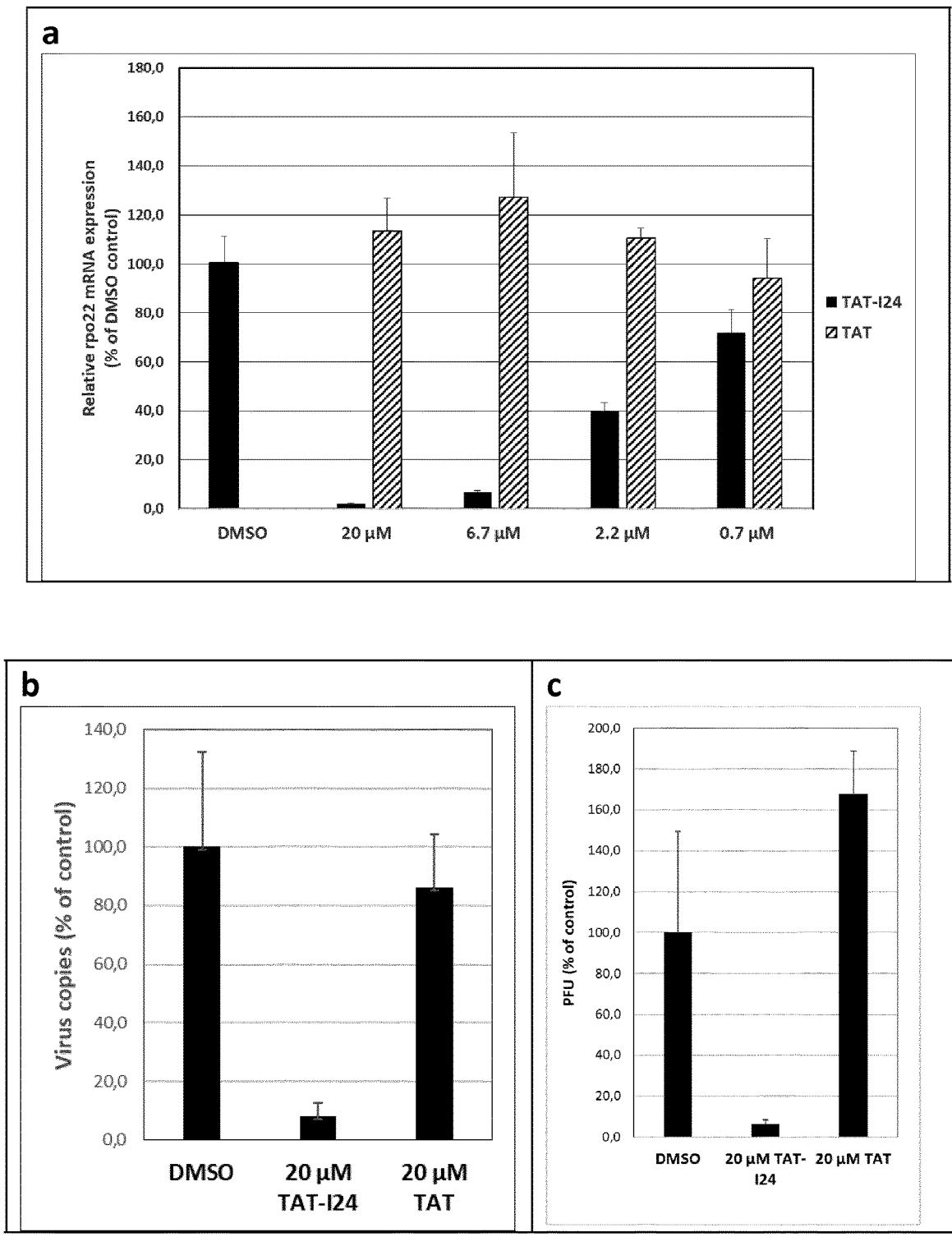
FIG. 9. TAT-I24 inhibits viral gene expression (a) and replication (b, c) of vaccinia virus in HEK293 cells.
Figure 10:
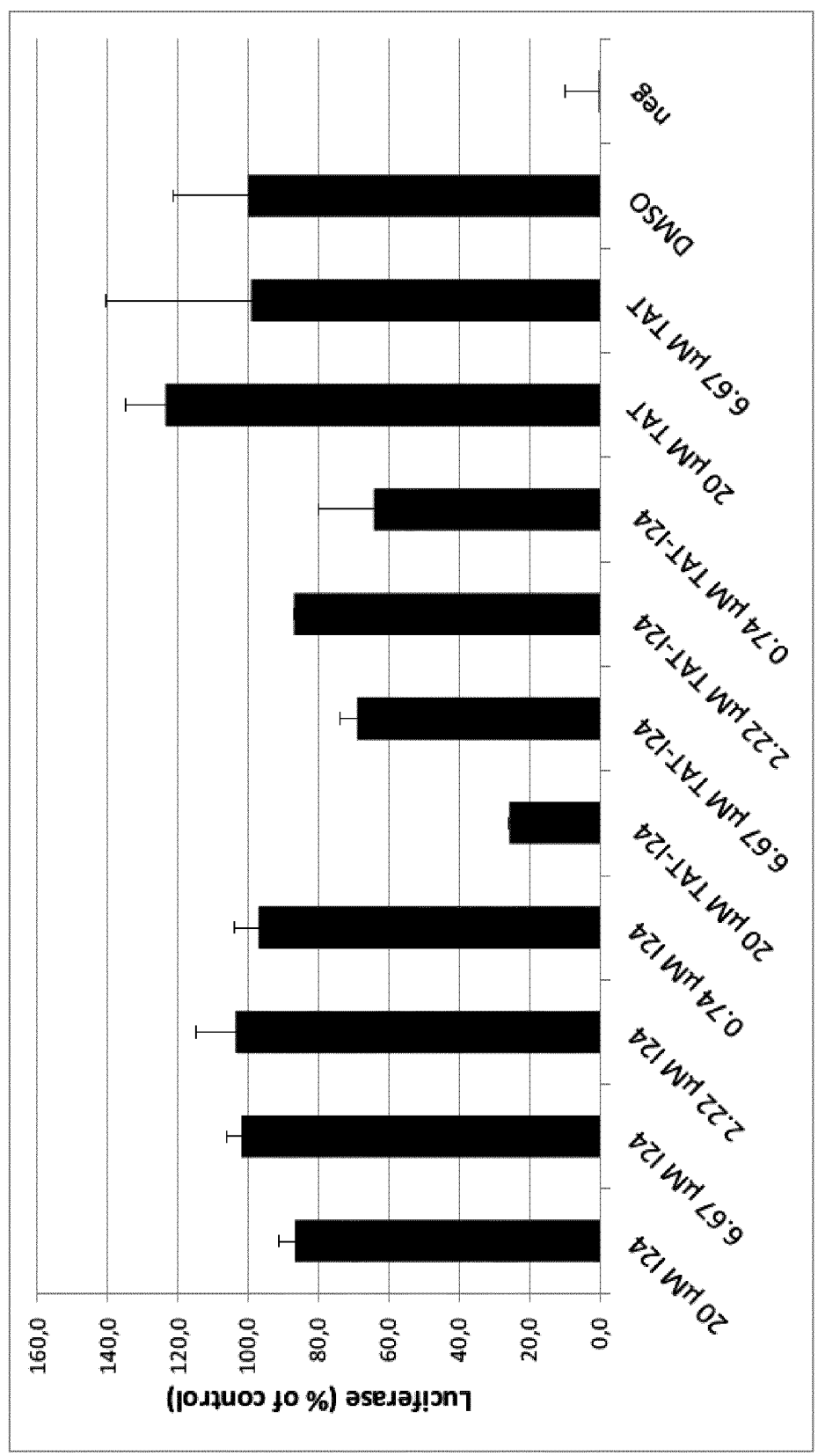
FIG. 10. TAT-I24 inhibits luciferase gene expression by a lentivirus.

Example 11: The Cell-Permeable Peptide I24 Inhibits Gene Expression by Lentivirus in HEK293 Cells HEK293 cells were incubated with peptide I24, TAT-tagged peptide I24 (TAT-I24), or TAT followed by addition of lentivirus containing luciferase under control of the CMV promoter for 48 hrs. Luciferase was downregulated by 75% in the presence of 20 µM TAT-I24 (FIG. 9).

Example 12: Inhibition of Reporter Gene Expression by Variants of the Peptide I24

A total of 29 peptides were synthesized. The peptides were applied to the transfection reaction together with the plasmid encoding luciferase and transfected into HEK293 cells. All peptides were tested at a final concentration of 2

µM and luciferase levels analysed 24 hrs post-transfection. Table 1 shows inhibition of reporter gene expression relative to the DMSO control.

TABLE 1

Effects of peptide variants on reporter gene expression in HEK293 in a transient transfection of plasmid-DNA.

| No. | Name | Sequence | Modification | luciferase % of DMSO con- | SEQ ID No. |
|---|---|---|---|---|---|
| 1 | TAT-I24 | GRKKRRQRRRPPQCLAFYACFC | TAT | 1.8 | 20 |
| 2 | I24 dimer | CLAFYACFCGGGCLAFYACFC | Dimer | 3.8 | 40 |
| 3 | I24 M20 | CLAFYACFWC | F8 C9insW | 5.6 | 2 |
| 4 | I24 M22 | CLAFYACLWC | F8L, F8 C9ins W | 6.8 | 3 |
| 5 | I24 M5 | CLAFYACFAC | F8 C8insA | 10.6 | 4 |
| 6 | I24 M12 | CLVFYACFC | A3V | 11.8 | 5 |
| 7 | I24 | CLAFYACFC | | 12.2 | 6 |
| 8 | I24 M17 | CLLYFCFC | A3L, F4Y, Y5F, A6del | 16.7 | 7 |
| 9 | I24 M11 | CAAFYACFC | L2A | 32.2 | 8 |
| 10 | I24 M6 | SLAFYACFAC | C1S, F8 C9nsA | 41.9 | 9 |
| 11 | I24 M29 | CLAFYARFC | C7R | 56.3 | 10 |
| 12 | I24 M14 | CLAFYCFAC | A6del, F8 C9insA | 63.2 | 11 |
| 13 | I24 M13 | CLAFYCFC | A6del | 64.9 | 12 |
| 14 | I24 M16 | CLAYFCFC | F4Y, Y5F, A6del | 68.7 | 13 |
| 15 | I24 M7 | SAFYACFAC | C1S, L2del, F8 C9insA | 75.9 | 41 |
| 16 | I24 M28 control | CLAFYRCFC DMSO | A6R | 93.4 100.0 | 42 |
| 17 | I24 M4 | SLAFYASFS | C1S, C7S, C9S | 100.5 | 43 |
| 18 | I24 M9 | FYACFC | C1 A3del | 103.6 | 44 |
| 19 | I24 M10 | FYACFAC | C1 A3del, F8 C9insA | 104.2 | 45 |
| 20 | I24 M18 | FYCFC | C1 A3del, A6del | 107.8 | 46 |
| 21 | I24 M2 | CLAFYAC | F8 C9del | 110.1 | 47 |
| 22 | I24 M27 | CLAFRACFC | Y5R | 110.9 | 48 |
| 23 | I24 M30 | CLAFYACRC | F8R | 116.5 | 49 |
| 24 | I24_M19 | FYCFAC | C1_A3del, A6del, F8_C9insA | 118.6 | 50 |
| 25 | I24 M26 | CLARYACFC | F4R | 128.6 | 51 |
| 26 | I24 M31 | SVFYACFC | M8variant: A8del | 135.5 | 52 |
| 27 | I24 M23 | CPSALAFYC | | 139.1 | 53 |
| 28 | | WSEQCFTCWW (Deng et al., 2004) | | 106.2 | 54 |
| 29 | I24_M8 | SVFYACFAC (similar to Deng et al., 2004) | | 103.7 | 55 |

Example 13: Inhibition of Colony Formation in Bacteria Transformed Simultaneously with a Plasmid-DNA Containing an Antibiotic Resistance-Gene and the Peptide I24

Figure 11:
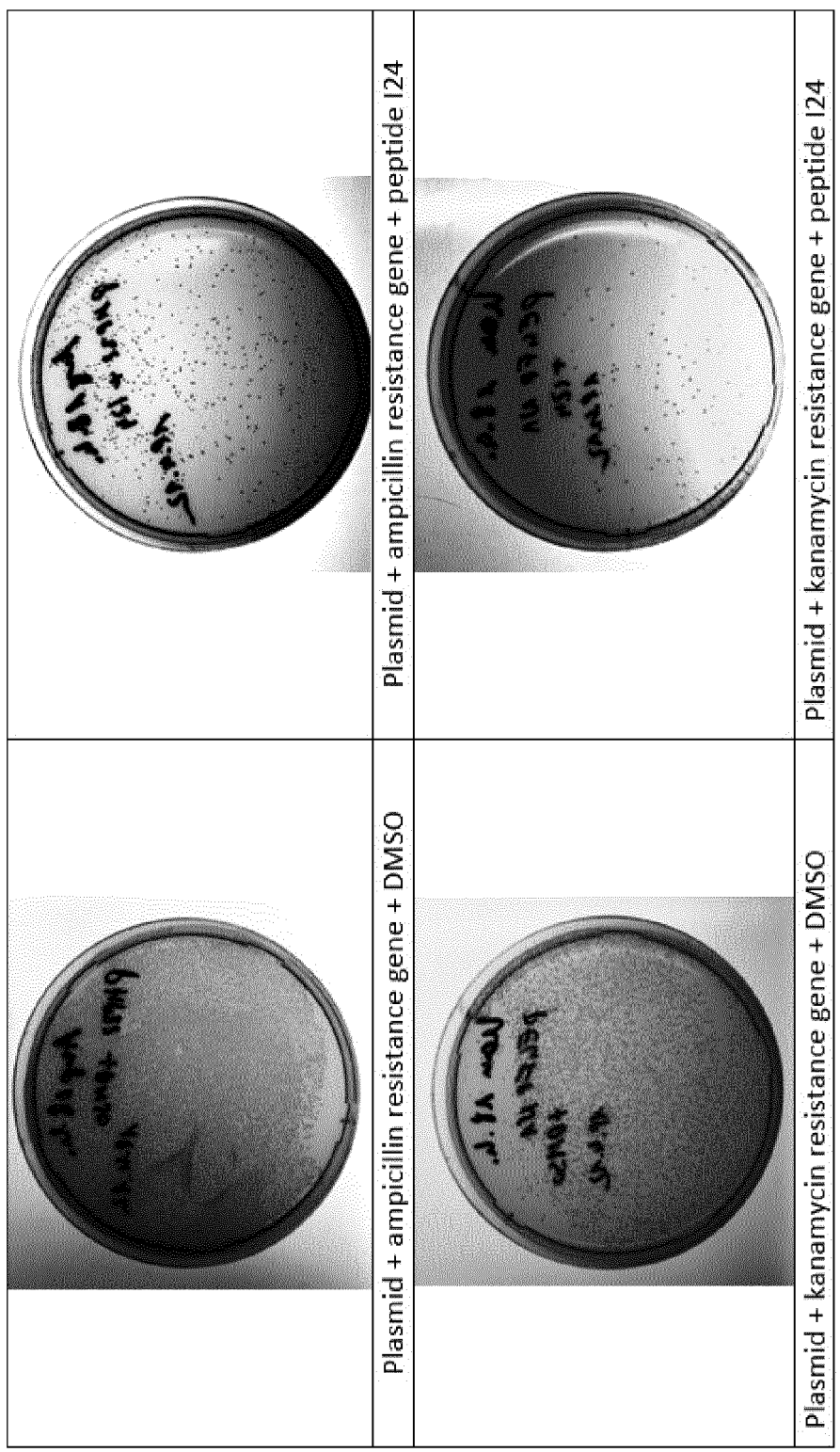
FIG. 11. Colony formation is inhibited in *E. coli* cells transformed simultaneously with plasmid and I24.

Competent *Escherichia coli* cells were transformed with a plasmid containing an ampicillin resistance gene or a kanamycin resistance gene and either DMSO as vehicle control or I24. On the next day, number of colonies was reduced in the presence of peptide I24 compared to the vehicle control (FIG. 11).

Example 14: Inhibition of Plasmid Replication and Beta-Lactamase mRNA Expression in *E. Coli* Cells Transformed with Plasmid and Peptide I24

Figure 12:
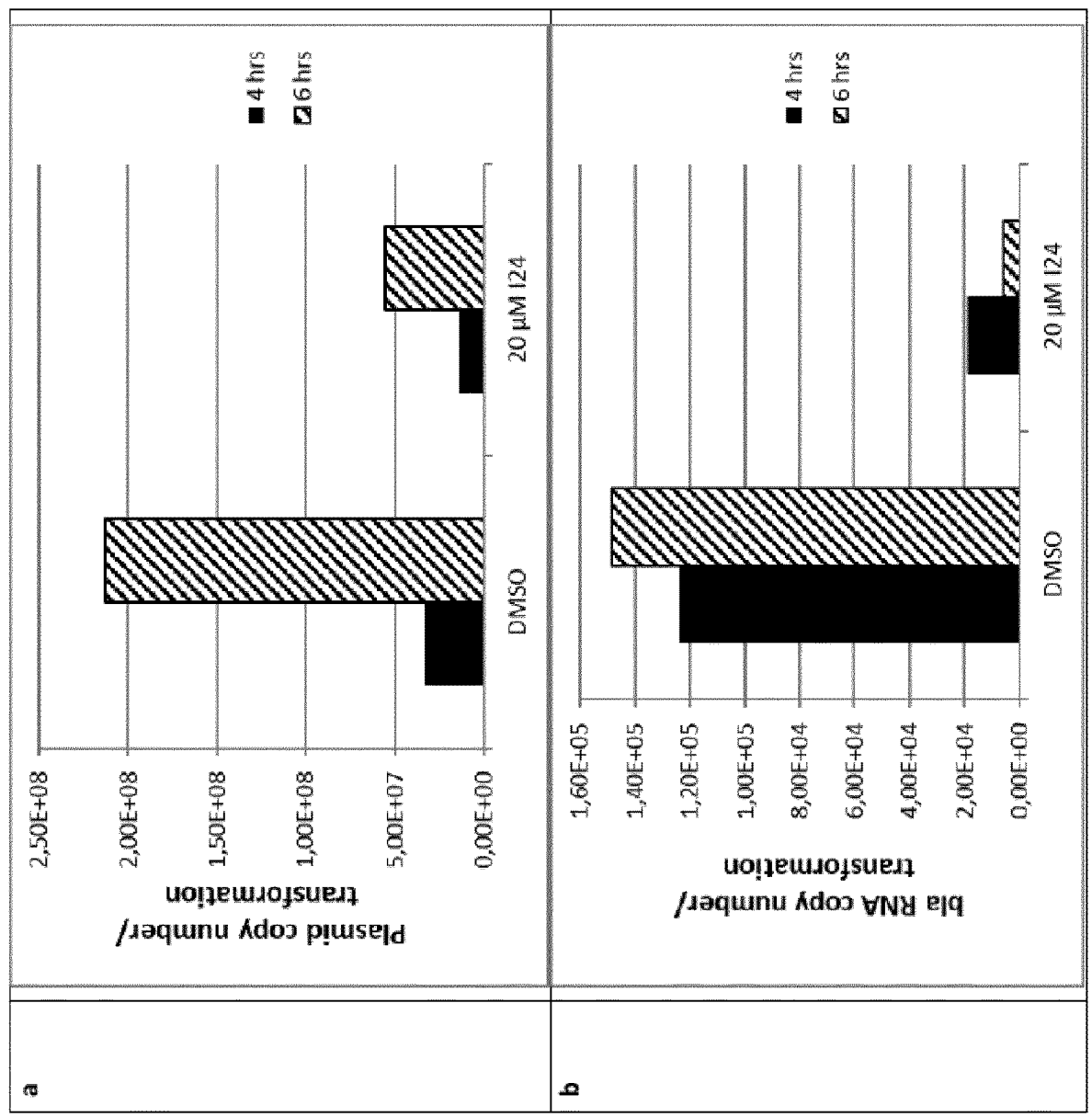
FIG. 12. Analysis of plasmid copy numbers in *E. coli* cells 4 and 6 hrs after transformation of plasmid-DNA in the presence of peptide I24 (a) and β-lactamase (bla) mRNA levels.

Competent *Escherichia coli* cells were transformed with a plasmid containing an ampicillin resistance gene and peptide I24. After indicated time-points, total plasmid numbers and β-lactamase mRNA levels were determined by real-time PCR normalized to an *E. coli* single-copy gene. Both, plasmid copy numbers and β-lactamase mRNA levels were downregulated in the presence of peptide I24 (FIG. 12).

Example 15: Comparative Data

A publication by Deng et al. (2004) described peptides which can inhibit DNA binding, transactivator and DNA replication of the human papillomavirus Type 11 E2 protein. The peptides were identified by a phage screen against the E2 protein. From the screening of group 1, one sequence SVFYACFACF from the biopanning has similarity with peptide I24, particularly the FYACF motif. Another peptide from the publication by Deng et al. has the sequence WSEQCFTCWW (Sequence 28 shown in Table 1). Both sequences were found only once in several biopanning rounds and no data on any biological activity is shown with these peptides in the publication. Based on sequence SVFYACFACF, specific amino acid residues were changed or included in the I24 variants (I24 M8 shown in Table 1). Other variations were insertions of W or A between F8 and C9 or change of F8 to L which did not impair activity of the peptide I24. Change of position A3 of I24 by V did not negatively affect potency, while replacement of C1 by S had some negative effect on potency. The peptides SVFYAC-FAC and WSEQCFTCWW exhibited no inhibitory effect in the cellular transfection assays when tested at 2 µM, a concentration at which I24 inhibits reporter gene expression by approximately 90%. However, Deng et al. did not provide any data on these two peptides and focussed on a third sequence from group 1 (EDGGSFMCLWCGEVHG; SEQ ID No. 57) which shows inhibitory effects on papillomavirus 11 E2 transactivation and replication functions. It is possible, that there exists a common mechanism of action between these peptides and peptide I24, but no data supporting an effect relating to inhibition of gene expression from "foreign" DNA which strongly supports the novelty of the findings obtained with I24. Deng et al. (2004) showed inhibition of E2-dependent reporter gene expression with the peptide EDGGSFMCLWCGEVHG (SEQ ID No. 57) expressed with a nuclear localization signal intracellularly but linked these effects to the interaction with the E2 protein. No other effects in living cells nor use of cell-penetrating peptides were shown in this study (Deng et al. 2004). In contrast, the peptides I24 or TAT-I24 are active without a nuclear localization signal only on the "foreign" DNA molecule and not on expression of cellular proteins and exert these effects upon direct application to the cells not shown in the publication by Deng et al. (2004) or any other publication known in the art.

Another sequence disclosed in patent application WO 2011/086116 (PSALAFY (SEQ ID NO: 58 in WO 2011/086116)) was also included. The peptide M23 with the sequence CPSALAFYC (SEQ ID No. 53), which has the motif LAFYC similar to I24, was inactive in the cellular transfection assay at a concentration up to 20 µM where I24 causes 90% inhibition of reporter gene expression.

Example 16: The Cell-Permeable Peptide I24 Inhibits Replication of Herpes Simplex Virus Cells were infected with herpes simplex virus and replication of virus determined by a plaque-formation assay (see examples above). Replication of herpes simplex virus was inhibited by TAT-I24 in a dose-dependent manner.

The invention claimed is:

1. A method of treating a disorder or disease associated with the transcription and/or translation of heterologous nucleic acid molecules in cells of a mammal or human individual comprising administering an effective amount of one or more peptides comprising or consisting of an amino acid sequence selected from the group consisting of CLAFYACFWC (SEQ ID No. 2), CLAFYACLWC (SEQ ID No. 3), CLAFYACFAC (SEQ ID No. 4), CLVFYACFC (SEQ ID No. 5), CLAFYACFC (SEQ ID No. 6), CLLYFCFC (SEQ ID No. 7), CAAFYACFC (SEQ ID No. 8), SLAFYACFAC (SEQ ID No. 9), CLAFYARFC (SEQ ID No. 10), CLAFYCFAC (SEQ ID No. 11), CLAFYCFC (SEQ ID No. 12), CLAYFCFC (SEQ ID No. 13).

2. The method of claim 1, wherein the one or more peptides comprise a peptidic compound comprising at least one peptide according to claim 1.

3. The method of claim 2, wherein the peptidic compound comprises 3 or 4 identical or different peptides.

4. The method of claim 2, wherein the peptidic compound is modified to exhibit cell-penetrating properties.

5. The method of claim 2, wherein the peptidic compound or the at least one peptide is fused C- and/or N-terminally to at least one cell-penetrating peptide.

6. The method of claim 5, wherein the at least one cell-penetrating peptide is selected from the group consisting of a TAT peptide and a polycationic tag.

7. The method of claim 5, wherein the at least one cell-penetrating peptide comprises or consists of an amino acid sequence selected from the group of HIV TAT protein comprising amino acid residues 37 to 72 of SEQ ID No. 14, GRKKRRQRRRPPQ (SEQ ID No. 15), YGRKKRRQRRR (SEQ ID No. 16), CYGRKKRRQRRR (SEQ ID No. 17), YGRKKRRQRRRGGG (SEQ ID No. 18), CGRKKRRQRRR (SEQ ID No. 19), TRSSRAGLQFPVGRVHRLLRK (SEQ ID NO: 26), GWTLNSAGYLLGKINLKALAALAKKIL (SEQ ID NO: 27), the KALA peptide comprising the sequence WEAK- LAKALAKALAKHLAKALAKALKACEA (SEQ ID NO: 28), MAP comprising the sequence KLALKLALKAL-KAALKLA (SEQ ID NO: 29), Pep-1 comprising the sequence KETWWETWWTEWSQPKKKRKV (SEQ ID NO: 30), hCT(9-32) comprising the sequence LGTYTQDFNKFHTFPQTAIGVGAP (SEQ ID NO: 31), pVEC comprising the sequence LLIILRRRIRKQAHAHSK (SEQ ID NO: 32), pISL comprising the sequence RVIR-VWFQNKRCKDKK (SEQ ID NO: 33), Erns comprising the sequence RQGAARVTSWLGRQLRIAGKRLEGRSK (SEQ ID NO: 34), Restrictocin L3comprising the sequence KLIKGRTPIKFGK (SEQ ID NO: 35); MPG comprising the sequence GALFLGFLGAAGSTMGAWSQPKSKRKV (SEQ ID NO: 36) GALFLGFLGAAGSTMGAWSQPK-SKRKV-cysteamide; SV-40 Large T-antigen Nuclear Localization Signal (NLS) comprising the sequences PKKKRKVEDPYC (SEQ ID No. 37), CGGGPKKKRKVED (SEQ ID NO: 38), Rabies Virus Glycoprotein (RVG) comprising the sequence YTIWMPENPRPGTPCDIFTNSRGKRASNG(SEQ ID NO: 39), and the Antennapedia protein homeodomain.

8. The method of claim 2, wherein the at least one peptide is fused or conjugated to a label.

9. The method according to claim 8, wherein the peptide is linear or cyclic.

10. The method of claim 8, wherein the label is selected from the group consisting of a dye, a fluorescent dye, a fluorescent protein, streptavidin, biotin, and a dye-binding peptide.

11. A method of treating a viral; or bacterial infection in a mammal or human individual comprising administering an effective amount of one or more peptides to a subject in need thereof, the one or more peptides comprising or consisting of an amino acid sequence are selected from the group consisting of CLAFYACFWC (SEQ ID No. 2), CLAFYA-CLWC (SEQ ID No. 3), CLAFYACFAC (SEQ ID No. 4), CLVFYACFC (SEQ ID No. 5), CLAFYACFC (SEQ ID No. 6), CLLYFCFC (SEQ ID No. 7), CAAFYACFC (SEQ ID No. 8), SLAFYACFAC (SEQ ID No. 9), CLAFYARFC (SEQ ID No. 10), CLAFYCFAC (SEQ ID No. 11), CLAFYCFC (SEQ ID No. 12), CLAYFCFC (SEQ ID No. 13).

12. The method according to claim 11, wherein the infection is a viral infection.

13. The method according to claim 11, wherein the treatment comprises preventing bacterial cells to gain genes or functional fragments thereof capable of providing antibiotic resistance to the bacterial cells.

14. A method of treating an infection by a DNA virus, comprising administering an effective amount of one or more peptides to a subject in need thereof, the one or more peptides comprising or consisting of an amino acid sequence selected from the group consisting of CLAFYACFWC (SEQ ID No. 2), CLAFYACLWC (SEQ ID No. 3), CLAFYAC-FAC (SEQ ID No. 4), CLVFYACFC (SEQ ID No. 5), CLAFYACFC (SEQ ID No. 6), CLLYFCFC (SEQ ID No. 7), CAAFYACFC (SEQ ID No. 8), SLAFYACFAC (SEQ ID No. 9), CLAFYARFC (SEQ ID No. 10), CLAFYCFAC (SEQ ID No. 11), CLAFYCFC (SEQ ID No. 12), CLAY-FCFC (SEQ ID No. 13).

15. A method for inhibiting transcription and/or translation of a heterologous nucleic acid molecule in a cell comprising contacting the heterologous nucleic acid molecule in vitro with one or more peptides peptides comprising or consisting of an amino acid sequence selected from the group consisting of CLAFYACFWC (SEQ ID No. 2), CLAFYACLWC (SEQ ID No. 3), CLAFYACFAC (SEQ ID No. 4), CLVFYACFC (SEQ ID No. 5), CLAFYACFC (SEQ ID No. 6), CLLYFCFC (SEQ ID No. 7), CAAFYACFC (SEQ ID No. 8), SLAFYACFAC (SEQ ID No. 9), CLAF-YARFC (SEQ ID No. 10), CLAFYCFAC (SEQ ID No. 11), CLAFYCFC (SEQ ID No. 12), CLAYFCFC (SEQ ID No. 13).

16. The method according to claim 15, wherein the heterologous nucleic acid molecule is of viral or bacterial origin.

17. The method according to claim 15, wherein the heterologous nucleic acid molecule contains nucleic acid stretches encoding antibiotic resistance genes or functional fragments thereof.

18. A method for preventing bacterial cells to gain genes or functional fragments thereof capable to provide antibiotic resistance to said bacterial cells comprising contacting the bacterial cells in vitro with one or more peptides comprising or consisting of an amino acid sequence selected from the group consisting of CLAFYACFWC (SEQ ID No. 2), CLAFYACLWC (SEQ ID No. 3), CLAFYACFAC (SEQ ID No. 4), CLVFYACFC (SEQ ID No. 5), CLAFYACFC (SEQ ID No. 6), CLLYFCFC (SEQ ID No. 7), CAAFYACFC (SEQ ID No. 8), SLAFYACFAC (SEQ ID No. 9), CLAF-YARFC (SEQ ID No. 10), CLAFYCFAC (SEQ ID No. 11), CLAFYCFC (SEQ ID No. 12), CLAYFCFC (SEQ ID No. 13).

19. A method for inhibiting or preventing viral spread in a cell culture comprising contacting the cell culture with one or more peptides comprising or consisting of an amino acid sequence selected from the group consisting of CLAFY-ACFWC (SEQ ID No. 2), CLAFYACLWC (SEQ ID No. 3), CLAFYACFAC (SEQ ID No. 4), CLVFYACFC (SEQ ID No. 5), CLAFYACFC (SEQ ID No. 6), CLLYFCFC (SEQ ID No. 7), CAAFYACFC (SEQ ID No. 8), SLAFYACFAC (SEQ ID No. 9), CLAFYARFC (SEQ ID No. 10), CLAFYCFAC (SEQ ID No. 11), CLAFYCFC (SEQ ID No. 12), CLAYFCFC (SEQ ID No. 13).

20. A method for inhibiting phage infection of bacteria by a phage comprising contacting the bacteria or phage in vitro with one or more peptides comprising or consisting of an amino acid sequence selected from the group consisting of CLAFYACFWC (SEQ ID No. 2), CLAFYACLWC (SEQ ID No. 3), CLAFYACFAC (SEQ ID No. 4), CLVFYACFC (SEQ ID No. 5), CLAFYACFC (SEQ ID No. 6), CLLY-FCFC (SEQ ID No. 7), CAAFYACFC (SEQ ID No. 8), SLAFYACFAC (SEQ ID No. 9), CLAFYARFC (SEQ ID No. 10), CLAFYCFAC (SEQ ID No. 11), CLAFYCFC (SEQ ID No. 12), CLAYFCFC (SEQ ID No. 13).

21. A method for localizing transcription and/or translation of a heterologous nucleic acid molecule within a eukaryotic cell comprising contacting the eukaryotic cell in vitro with one or more peptidic compounds comprising at least one peptide fused or conjugated to a label, the at least one peptide comprising or consisting of an amino acid sequence selected from the group consisting of CLAFY-ACFWC (SEQ ID No. 2), CLAFYACLWC (SEQ ID No. 3), CLAFYACFAC (SEQ ID No. 4), CLVFYACFC (SEQ ID No. 5), CLAFYACFC (SEQ ID No. 6), CLLYFCFC (SEQ ID No. 7), CAAFYACFC (SEQ ID No. 8), SLAFYACFAC (SEQ ID No. 9), CLAFYARFC (SEQ ID No. 10), CLAFYCFAC (SEQ ID No. 11), CLAFYCFC (SEQ ID No. 12), CLAYFCFC (SEQ ID No. 13).

22. The method according to claim 21, wherein the heterologous nucleic acid molecule is of viral or bacterial origin.

* * * * *